(12) United States Patent
Presta et al.

(10) Patent No.: US 8,303,955 B2
(45) Date of Patent: Nov. 6, 2012

(54) HUMANIZED ANTI-CD40 ANTIBODIES AND THEIR METHODS OF USE

(75) Inventors: Leonard G. Presta, San Francisco, CA (US); Lori Y. O'Connell, Montara, CA (US); Svetlana O. Doronina, Snohomish, WA (US)

(73) Assignee: Seattle Genetics, Inc., Bothell, WA (US)

( * ) Notice: Subject to any disclaimer, the term of this patent is extended or adjusted under 35 U.S.C. 154(b) by 857 days.

(21) Appl. No.: 11/913,305

(22) PCT Filed: May 26, 2006

(86) PCT No.: PCT/US2006/020688
§ 371 (c)(1),
(2), (4) Date: Oct. 24, 2008

(87) PCT Pub. No.: WO2006/128103
PCT Pub. Date: Nov. 30, 2006

(65) Prior Publication Data
US 2009/0181015 A1 Jul. 16, 2009

Related U.S. Application Data

(60) Provisional application No. 60/684,853, filed on May 26, 2005.

(51) Int. Cl.
*A61K 39/395* (2006.01)
*C07K 16/28* (2006.01)
(52) U.S. Cl. ............... 424/153.1; 424/130.1; 424/133.1; 424/141.1; 424/143.1; 424/144.1; 424/173.1; 530/387.1; 530/387.3; 530/388.2; 530/388.22; 530/388.7; 530/388.73
(58) Field of Classification Search .................. None
See application file for complete search history.

(56) References Cited

U.S. PATENT DOCUMENTS

| | | | | |
|---|---|---|---|---|
| 5,182,368 A | 1/1993 | Ledbetter et al. | ......... | 530/388.73 |
| 5,354,847 A | 10/1994 | Liu et al. | ..................... | 530/387.3 |
| 5,530,101 A | 6/1996 | Queen et al. | ................ | 530/387.3 |
| 5,540,926 A | 7/1996 | Aruffo et al. | .............. | 424/153.1 |
| 5,597,569 A | 1/1997 | Siegall et al. | .............. | 424/183.1 |
| 5,674,492 A | 10/1997 | Armitage et al. | .......... | 424/144.1 |
| 5,677,165 A | 10/1997 | De Boer et al. | ............ | 435/343.1 |
| 5,872,215 A | 2/1999 | Osbourne et al. | .......... | 530/387.3 |
| 5,874,082 A | 2/1999 | De Boer | ..................... | 424/153.1 |
| 5,876,950 A * | 3/1999 | Siadak et al. | ................ | 435/7.23 |
| 5,985,847 A | 11/1999 | Carson et al. | .................... | 514/44 |
| 6,037,454 A | 3/2000 | Jardieu et al. | ............. | 530/387.3 |
| 6,054,297 A | 4/2000 | Carter et al. | ................ | 435/69.6 |
| 6,056,959 A | 5/2000 | De Boer et al. | ............ | 424/178.1 |
| 6,828,121 B2* | 12/2004 | Chen | ............................ | 435/69.1 |
| 6,838,261 B1 | 1/2005 | Siegall et al. | .............. | 435/69.6 |
| 6,843,989 B1 | 1/2005 | Siegall et al. | ............. | 424/130.1 |
| 6,946,129 B1 | 9/2005 | Siegall et al. | ............. | 424/130.1 |
| 7,329,737 B2* | 2/2008 | Sexton et al. | ........... | 530/388.25 |
| 7,601,335 B2* | 10/2009 | McCutcheon et al. | ........ | 424/9.2 |
| 7,662,387 B2* | 2/2010 | Law et al. | .................. | 424/178.1 |
| 2003/0022860 A1* | 1/2003 | Melief et al. | ..................... | 514/44 |
| 2006/0003412 A1 | 1/2006 | Chamberlain et al. | ....... | 435/69.1 |
| 2006/0008883 A1 | 1/2006 | Lazar et al. | .................. | 435/69.7 |

FOREIGN PATENT DOCUMENTS

| | | |
|---|---|---|
| JP | 2002/503495 A | 2/2002 |
| JP | 2003519470 A | 6/2003 |
| JP | 2003/527861 A | 9/2003 |
| WO | WO 95/17202 | 6/1995 |
| WO | WO 96/18413 | 6/1996 |
| WO | WO 97/31025 A1 | 8/1997 |
| WO | WO 98/33810 | 8/1998 |
| WO | WO 99/42075 A2 | 8/1999 |
| WO | WO 00/75348 A1 | 12/2000 |
| WO | WO 01/70984 A2 | 9/2001 |

OTHER PUBLICATIONS

Rudikoff et al.,Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Accession No. C29380, 1988.
Accession No. 69899, 1997.
Accession No. S67941, 1997.
Accession No. W78434, 1998.
Accession No. Y06716, 1999.
Ada, G., "The coming of age of immunotherapy," Immunology and Cell Biology, 1999, 77, p. 180-185.
Alessandrini, A. et al., "Coordination of immunoglobulin $DJ_H$ transcription and D-to-$J_H$ rearrangement by promoter-enhancer approximation," *Mol. Cell Biol.*, 1991, 11(4), 2096-2107.
Andersen et al., "Soluble CD40 ligang induces cell cycle progression in primary mantle cell lymphoma," Blood, 1999, 94(10), Suppl. 1, p. 630a.
Apostolopoulos et al., "MUC1 cross-reactive Galα(1,3)Gal antibodies in humans switch immune response from cellular to humoral," Nature Medicine, 1998, 4, 315-320.
Armitage et al., "Distinct patterns of inhibition by CD40 mAb of the CD40 ligand-CD40 interaction," *Leukocyte Typing V*, Schlossman et al. (eds.), 1995, 1, 551-552.
Becker et al., "Tumor escape mechanisms from immunosurveillance: induction of unresponsiveness in a specific MHC-restricted $CD4^+$ human T cell clone by the autologous MHCclass $II^+$melanoma," *International Immunology*, 1993, 5(12), 1501-1508.
Bender et al., Human antibodies and Hybridomas, 1993, 4, 74-79 (Absrtact).
Bjorck et al., "Antibodies to distinct epitopes on the CD40 molecule co-operate in stimulation and can be used for the detection of soluble CD40," *Immunology*, 1994, 83, 430-437.
Bjorck, P. et al., "CD40 antibodies defining distinct epitopes display qualitative differences in their induction of B-cell differentiation," *Immunology*, 1996, 87(2), 291-295.

(Continued)

Primary Examiner — Phillip Gambel
(74) Attorney, Agent, or Firm — Seattle Genetics, Inc.

(57) ABSTRACT

Provided are humanized anti-CD40 antibodies and antigen-binding fragments and methods for treating disease characterized by expression of CD40 antigen.

20 Claims, 5 Drawing Sheets

OTHER PUBLICATIONS

Bridges et al., "Selective in Vivo Antitumor Effects of Monoclonal Anti-I-A Antibody on a B Cell Lymphoma," J. Immumol., 1987, 139(12), 4242-4249.

Bubenik, J. et al., "Monoclonal antibodies against human urinary bladder carcinomas: selectivity and utilization for gamma scintigraphy," Eur. J. Cancer Clin. Oncol., 1985, 21(6), 701-710.

Buchsbaum et al., "Improved Delivery of Radiolabeled Anti-B1 Monoclonal Antibody to Raji Lymphoma Xenografts by Predosing withUnlabeled Anti-B1 Monoclonal Antibody," Cancer Research, 1992, 52, 637-642.

Buhmann et al., "CD40-Activated B-cell Chronic Lymphocytic Leukemia Cells for Tumor Immunotherapy: Stimulation of Allogeneic Versus Autologous T Cells Generates Different Types of Effector Cells," Blood, 1999, 93, p. 1992-2002.

Carter et al., "Humanization of an anti-p185$^{HER2}$ antibody for human cancer therapy," Proc. Natl. Acad. Sci. USA, 1992, 89, 4285-4289.

Cattan et al., "The C.B.17 SCID Mouse Strain as a Model for Human Disseminated Leukemia and Myeloma In Vivo," Leukemia Research, 1994, 18(7), 513-522.

Caux et al., "Activation of Human Dendritic Cells through CD40 Cross-Linking," Journal of Experimental Medicine, 1994, 180, p. 1263-1272.

Cella et al., "Ligation of CD40 on Dendritic Cells Triggers Production of High Levels of Interleukin-12 and Enhances T Cell Stimulatory Capacity: T-T Help via APC Activation," Journal of Experimental Medicine, 1996, 184, p. 747-752.

Challa, A. et al., "Epitope-dependent synergism and antagonism between CD40 antibodies and soluble CD40 ligand for the regulation of CD23 expression and lgE synthesis in human B cells," Allergy, 1999, 54(6), 576-583.

Chen et al., "Nucleotide and translated amino acid sequences of cDNA coding for the variable regions of the light and heavy chains of mouse hybridoma antibodies to blood group A and B substances," J. Biol. Chem., 1987, 262(28), 13579-13583.

Clark, E.A. et al., "Activation of human B cells mediated through two distinct cell surface differentiation antigens, Bp35 and Bp50," PNAS U.S.A., 1986, 83(12), 4494-4498.

Clothia et al., "Canonical Structures for the Hypervariable Regions of Immunoglobulins," J. Mol. Biol., 1987, 196, 901-917.

Clothia et at, "Domain Association in Immunoglobulin Molecules: The Packing of Variable Domains," J. Mol. Biol., 1985, 186, 651-663.

Costello et al., "Tumor Escape from Immune Surveillance," Archivum Immunologiae et Therapiae Experimentalis, 1999, 47, p. 83-88.

Cunningham et al., "Receptor and Antibody Epitopes in Human Growth Hormone Identified by Homolog-Scanning Mutagenesis," Science, 1989, 243, 1330-1336.

De Paoli, P., "High CD40 membrane expression in AIDS-related lymphoma B cell lines is associated with the CD45RA+, CD45RO+, CD95+ phenotype and high levels of its soluble form in culture supernatants," Cytometry, 1997, 30(1), 33-38.

Fanslow et al., "CD40 mAb M2 and M3 inhibit CD40 ligand binding and function," Leukocyte Typing V, 1995, Schlossman et al. (eds.), 1, 555-556.

Francisco, JA et al., "Construction, expression, and characterization of BD1-G28-5 sFv, a single-chain anti-CD40 immunotoxin containing the ribosome-inactivating protein bryodin 1," J. Biol. Chem., 1997, 272(39), 24165-24169.

Frisch et al., "A Soluble Immunoglobulin Variable Domain without a Disulfide Bridge," Biol. Chem., 1994, Hoppe-Seyler, 375, 353-356.

Funakoshi, S. et al., "Differential in vitro and in vivo antitumor effects mediated by anti-CD40 and anti-CD20 monoclonal antibodies against human B-cell lymphomas," J. Immunother Emphasis Tumor Immunol., 1996, 19(2), 93-101.

Funakoshi, S. et al., "Inhibition of human B-cell lymphoma growth by CD40 simulation," Blood, 1994, 83(10), 2787-94.

Ghetie et al., "Disseminated or Localized Growth of a Human B-Cell Tumor (Daudi) in SCID Mice," Int. J. Cancer, 1990, 45, p. 481-485.

Gilliland, L.K. et al., "Rapid and reliable cloning of antibody variable regions and generation of recombinant single chain antibody fragments," Tissue Antigens, 1996, 47(1), 1-20.

Grafton, G. et al., "Mechanisms of antigen receptor-dependent apoptosis of human B lymphoma cells probed with a panel of 27 monoclonal antibodies," Cell Immunol., 1997, 182(1), 45-56.

Greenwood et al., "Effector functions of matched sets of recombinant human IgG subclass antibodies," Protein Engineering of Antibody Molecules for Prophylactic and Therapeutic Applications in Man., Clark (ed.), 1993, 85-100.

Grewal, IS et al., "CD40 and CD154 in cell-mediated immunity," Annu. Rev. Immunol., 1998, 16, 111-135.

Gura, T., "Systems for identifying new drugs are often faulty," Science, 1997, 278, 1041-1042.

Herbert et al., "Inhibition of specific antibody production by CD40L and a panel of antibodies to CD40," Leukocyte Typing V, 1995, Schlossman et al. (eds.), 1, 552-554.

Henriquez et al., "Differential Response to CD40 Litigation Among Burkitt Lymphoma Lines That Are Uniformly Responsive to Epstein-barr Virus Latent Membrane Protein 1$^1$," Journal of Immunology, 1999, 162, 3298-3307.

Hiraki et al., "Loss of HLA Haplotype in Lung Cancer Cell Lines: Implications for Immunosurveillance of Altered HLA Class I/II Phenotypes in Cancer," Clinical Cancer Research, 1999, 5, 933-936.

Hirano et al., "Inhibition of Human Breast Carcinoma Growth by a Soluble Recombinant Human CD40 Ligand," Blood, 1999, 93(9), 2999-3007.

Kaminski et al., "Pivotal Study of Iodine 1 131 Tositumomab for Chemotherapy-Refractory Low-Grade of Transformed Low-Grade B-Cell Non-Hodgkin's Lymphomas," J. of Clinical Oncology, 2001, 19(19), 3918-3928.

Katira et al, "CD40 Workshop Panel report," Leukocyte Typing V, 1995, Schlossman et al. (eds.), 1, 547-550.

Katira et al., "Identification of co-operative epitopes on CD40 supports the existence of a second CD40 ligand," Leukocyte Typing V, 1995, Schlossman et al. (eds.), 1, 547-550.

Kawabe et al., "Generation and characterization of CD40-deficient mice," Leukocyte Typing V, 1995, Schlossman et al. (eds.), 1, 550-551.

Kawaguchi et al., Proc. Ann. Meet. Am. Assoc. Cancer Res., 1997, 38, p. A2319 (Abstract).

Kawata et al., "Establishment of New SCID and Nude Mouse Models of Human B-Leukemia/Lymphoma and Effective Therapy of the Tumors with Immunotoxin and Monoclonal Antibody: Marked Difference between the SCID and Nude Mouse Models in the Antitumor Efficacy of Monoclonal Antibody," Cancer Research, 1994, 54, 2688-2694.

Kehry, MR, "CD40-mediated signaling in B cells, Balancing cell survival, growth, and death," J. Immunol., 1996, 156(7), 2345-2348.

Kim et al., "Restoring allosterism with compensatory mutations in hemoglobin," PNAS, 1994, 91, 11547-11551.

Koho, H. et al., "Monoclonal antibodies to antigens associated with transitional cell carcinoma of the human urinary bladder," Cancer Immunol. Immunother., 1984, 17, 165-172.

Kuhne, M.R. et al., "Assembly and regulation of the CD40 receptor complex in human B cells," J. Exp. Med., 1997, 186(2), 337-342.

Kwekkeboom et al., "CD40 plays an essential role in the activation of human B cells by murine EL4B5," Immunology, 1993, 79, 439-444.

Ledbetter et al., "Augmentation of normal and malignant B Cell Proliferation by Monoclonal antibody to the b cell-specific antigen BP50 (CDW40)$^1$," J. Immunol., 1987, 138(3), 788-794.

Malik, N. et al, "Activation of human monocytes through CD40 induces matrix metalloproteinases," J. Immunol., 1996, 156(10), 3952-3960.

Matthews, B., "Genetic and Structural Analysis of the Protein Stability Problem," Perspectives in Biochemistry, 1989, 2, 6-9.

Matsui et al., "A model for CD+8 CTL tumor immunosurveillance and regulation of tumor escape by CD+4 cells," J. Immunology, 1999, 163, p. 184-193.

Murphy, WJ et al., "Antibodies to CD40 prevent Epstein-Barr virus-mediated human B-cell lymphomagenesis in severe combined immune deficient mice given human peripheral blood lymphocytes," Blood, 1995, 86(5), 1946-1953.

Noelle, RJ et al., "A 39-kDa protein on activated helper T cells binds CD40 and transduces the signal for cognate activation of B cells," PNAS U.S.A., 1992, 89(14), 6550-6554.

Ostrowski et al., "Inhibition of Angiogenesis in the Treatment of Tumors," Archivum Immunologiae et Therapiae Experimentalis, 2001, 49, 27-31.

Paulie et al., "Monoclonal antibodies to antigens associated with transitional cell carcinoma of the human urinary bladder," Cancer Immunol. Immunother., 1984, 17, 173-179.

Paulie et al., "The Human B Lymphocyte and Carcinoma Antigen, CDw40, Is a Phosphoprotein Involved in Growth Signal Transduction," J. Immunol., 2000, 142(2), 590-595.

Pellat-Decounynck et al., "Expression of CD28 and CD40 in Human Myeloma Cells: A Comparative Study with Normal Plasma Cells," Blood, 1994, 84(8), 2597-2603.

Pound, JD et al., "Minimal cross-linking and epitope requirements for CD40-dependent suppression of apoptosis contrast with those for promotion of the cell cycle and homotypic adhesions in human B cells," Int. Immunol., 1999, 11(1), 11-20.

Riechmann et al., "Reshaping human antibodies for therapy," Nature, 1988, 332, 323-327.

Schlom, Jeffery., "Monoclonal Antibodies: They're More and Less Than You Think," Molecular Foundation of Oncology, Broader, S. (ed.), 1991, 95-134.

Schultze et al., Blood, 1996, 88(10), Suppl. 1, part 1-2, p. 162A (Abstract).

Schultze, J.L., "T-Cell-Mediated Immunity against B-Cell Malignancies: Preclinical Results and Translation into a Novel Immunotherapeutic Approach for B-Cell Maglignancies," Haematology and Blood Transfusion, 1998, 39, 716-731.

Sotomayor et al., Blood, 1998, 92(10). Suppl. 1, part 1-2, p. 541A.

Speiser, DE et al, "A regulatory role for TRAF1 in antigen-induced apoptosis of T cells," J Exp. Med., 1997, 185(10), 1777-1783.

Stamenkovic, I. et al., "A B-lymphocyte activation molecule related to the nerve growth factor receptor and induced by cytokines in carcinomas," EMBO J., 1989, 8(5), 1403-1410.

Tillman et al., "Both IgM and IgG Anti-DNA Antibodies are the Products of Clonally Selective B Cell Stimulation in (NZB×NZW)$F_1$ Mice," J. Exp. Med., 1992, 176(3), 761-769.

Tutt, AL et al., "Monoclonal Antibody Therapy of B cell Lymphoma: Signaling Activity on Tumor Cells Appears More Important Than Recruitment of Effectors," J. Immunol., 1998, 161(6), 3176-3185.

Uckun et al., "Temporal association of CD40 antigen expression with discreet stages of human B-cell ontogeny and the efficacy of the anti-CD40 immunotoxins," Blood, 1990, 76, 2449-2456 (abstract only).

Van Kooten, C. et al., "Functions of CD40 on B cells, dendritic cells and other cells," Curr. Opin. Immunol., 1997, 9(3), 330-337.

Vonderheide et al., "CD40 ligation of solid tumors does not induce the surgace phenotype characteristic of professional antigen presenting cells," Proceed. Amer. Assoc. Cancer Research, 1999, 40, p. 472.

Yeh, W.C. et al., "Early Lethality Functional NF-$_k$B Activation, and Increased Sensitivity to TNF-Induced Cell Death in TRAF2-Deficient Mice," Immunity, 1997, 7, 715-725.

Younes, A et al., "Elevated levels of biologically active soluble CD40 ligand in the serum of patients with chronic lymphocytic leukaemia," Br. J. Haematology, 1998, 100, 135-141.

International Nonproprietary Names for Pharmaceutical Substances (INN), WHO Drug Information, 2003, pp. 115-142, vol. 17, No. 2, [online] [Retrieved on Oct. 24, 2008] Retrieved from the Internet, URL: whglibdoc.who.int/druginfo/INN__2003__list49.pdf.

Francisco et al., "Agonistic Properties and in Vivo Antitumor Activity of the Anti-CD40 Antibody SGN-14," Cancer Research, 2000, vol. 60, pp. 3225-3231.

Kelly et al., "Preclinical pharmacokinetics, pharmacodynamics, and activity of humanized anti-CD40 antibody (SGN-40) in rodents and non-human primates," British Journal of Phamacology, 2006, vol. 148, pp. 1116-1123.

Tai et al., "Immunomodulatory Drug Lenalidomide (CC-5013, IMiD3) Augments Anti-CD40 SGN-40-Induced Cytotoxicity in Human Multiple Myeloma: Clinical Implications," Cancer Res, 2005, vol. 65, No. 24, pp. 11712-11720.

Tai et al., "Mechanisms by which SGN-40, a Humanized Anti-CD40 Antibody, Induces Cytotoxity in Human Multiple Myeloma Cells: Clinical Implications," Cancer Research, 2004, vol. 64, pp. 2846-2852.

WHO Drug Information, "International Nonproprietary Names for Pharmaceutical Substances (INN)," 2008, vol. 22, No. 3.

Hayashi et al., Recombinant humanized anti-CD40 monoclonal antibody triggers autologous antibody-dependent cell-mediated cytotoxicity against multiple myeloma cells, British Journal of Haematology, 2003, vol. 121, pp. 592-596.

* cited by examiner

```
                                                                          Variable Region
                                                                          ~~~~~~~~~~~~~~~
                               Leader Sequence
      ~~~~~~~~~~~~~~~~~~~~~~~~~~~~~~~~~~~~~~~~~~~~~~~~~~~~~~~~~~~~~~~
       M   G   W   S   C   I   I   L   F   L   V   A   T   A   T   G   V   H   S   E   V   Q   L   V  ·
  1   ATGGGATGGT CATGTATCAT CCTTTTTCTA GTAGCAACTG CAACTGGAGT ACATTCAGAA GTTCAGCTGG
       TACCCTACCA GTACATAGTA GGAAAAAGAT CATCGTTGAC GTTGACCTCA TGTAAGTCTT CAAGTCGACC
                                Variable Region
      ~~~~~~~~~~~~~~~~~~~~~~~~~~~~~~~~~~~~~~~~~~~~~~~~~~~~~~~~~~~~~~~~~~~~~~~~~~~~~~~~~
       ·  E   S   G   G   G   L   V   Q   P   G   G   S   L   R   L   S   C   A   A   S   G   Y   S  ·
 71   TGGAGTCTGG CGGTGGCCTG GTGCAGCCAG GGGGCTCACT CCGTTTGTCC TGTGCAGCTT CTGGCTACAG
       ACCTCAGACC GCCACCGGAC CACGTCGGTC CCCGAGTGA  GGCAAACAGG ACACGTCGAA GACCGATGTC
                                Variable Region
      ~~~~~~~~~~~~~~~~~~~~~~~~~~~~~~~~~~~~~~~~~~~~~~~~~~~~~~~~~~~~~~~~~~~~~~~~~~~~~~~~~
       ·  F   T   G   Y   Y   I   H   W   V   R   Q   A   P   G   K   G   L   E   W   V   A   R   V
 141  CTTCACCGGT TATTACATCC ACTGGGTCCG TCAGGCCCCG GGTAAGGGCC TGGAATGGGT TGCAAGGGTT
       GAAGTGGCCA ATAATGTAGG TGACCCAGGC AGTCCGGGGC CCATTCCCGG ACCTTACCCA ACGTTCCCAA
                                Variable Region
      ~~~~~~~~~~~~~~~~~~~~~~~~~~~~~~~~~~~~~~~~~~~~~~~~~~~~~~~~~~~~~~~~~~~~~~~~~~~~~~~~~
       I   P   N   A   G   G   T   S   Y   N   Q   K   F   K   G   R   F   T   L   S   V   D   N   S  ·
 211  ATTCCTAACG CCGGCGGTAC CAGTTATAAC CAGAAGTTCA AGGGCCGTTT CACATTGAGC GTCGACAATT
       TAAGGATTGC GGCCGCCATG GTCAATATTG GTCTTCAAGT TCCCGGCAAA GTGTAACTCG CAGCTGTTAA
                                Variable Region
      ~~~~~~~~~~~~~~~~~~~~~~~~~~~~~~~~~~~~~~~~~~~~~~~~~~~~~~~~~~~~~~~~~~~~~~~~~~~~~~~~~
       ·  K   N   T   A   Y   L   Q   M   N   S   L   R   A   E   D   T   A   V   Y   Y   C   A   R  ·
 281  CCAAAAACAC AGCATACCTG CAGATGAACA GCCTGCGTGC TGAGGACACT GCCGTCTATT ATTGTGCTCG
       GGTTTTTGTG TCGTATGGAC GTCTACTTGT CGGACGCACG ACTCCTGTGA CGGCAGATAA TAACACGAGC
                                                                          Human G1 Constant Region
                                                                          ~~~~~~~~~~~~~~~~~~~~~~~~~
                                Variable Region
      ~~~~~~~~~~~~~~~~~~~~~~~~~~~~~~~~~~~~~~~~~~~~~~~~~~~~~~~~~~~~~~~~~
       ·  E   G   I   Y   W   W   G   Q   G   T   L   V   T   V   S   S   A   S   T   K   G   P   S
 351  AGAGGGTATC TACTGGTGGG GTCAAGGAAC CCTGGTCACC GTCTCCTCGG CCTCCACCAA GGGCCCATCG
       TCTCCCATAG ATGACCACCC CAGTTCCTTG GGACCAGTGG CAGAGGAGCC GGAGGTGGTT CCCGGGTAGC
                               Human G1 Constant Region
      ~~~~~~~~~~~~~~~~~~~~~~~~~~~~~~~~~~~~~~~~~~~~~~~~~~~~~~~~~~~~~~~~~~~~~~~~~~~~~~~~~
       V   F   P   L   A   P   S   S   K   S   T   S   G   G   T   A   A   L   G   C   L   V   K   D  ·
 421  GTCTTCCCCC TGGCACCCTC CTCCAAGAGC ACCTCTGGGG GCACAGCGGC CCTGGGCTGC CTGGTCAAGG
       CAGAAGGGGG ACCGTGGGAG GAGGTTCTCG TGGAGACCCC CGTGTCGCCG GGACCCGACG GACCAGTTCC
                               Human G1 Constant Region
      ~~~~~~~~~~~~~~~~~~~~~~~~~~~~~~~~~~~~~~~~~~~~~~~~~~~~~~~~~~~~~~~~~~~~~~~~~~~~~~~~~
       ·  Y   F   P   E   P   V   T   V   S   W   N   S   G   A   L   T   S   G   V   H   T   F   P  ·
 491  ACTACTTCCC CGAACCGGTG ACGGTGTCGT GGAACTCAGG CGCCCTGACC AGCGGCGTGC ACACCTTCCC
       TGATGAAGGG GCTTGGCCAC TGCCACAGCA CCTTGAGTCC GCGGGACTGG TCGCCGCACG TGTGGAAGGG
                               Human G1 Constant Region
      ~~~~~~~~~~~~~~~~~~~~~~~~~~~~~~~~~~~~~~~~~~~~~~~~~~~~~~~~~~~~~~~~~~~~~~~~~~~~~~~~~
       ·  A   V   L   Q   S   S   G   L   Y   S   L   S   S   V   V   T   V   P   S   S   S   L   G
 561  GGCTGTCCTA CAGTCCTCAG GACTCTACTC CCTCAGCAGC GTGGTGACTG TGCCCTCTAG CAGCTTGGGC
       CCGACAGGAT GTCAGGAGTC CTGAGATGAG GGAGTCGTCG CACCACTGAC ACGGGAGATC GTCGAACCCG
                               Human G1 Constant Region
      ~~~~~~~~~~~~~~~~~~~~~~~~~~~~~~~~~~~~~~~~~~~~~~~~~~~~~~~~~~~~~~~~~~~~~~~~~~~~~~~~~
       T   Q   T   Y   I   C   N   V   N   H   K   P   S   N   T   K   V   D   K   K   V   E   P   K  ·
 631  ACCCAGACCT ACATCTGCAA CGTGAATCAC AAGCCCAGCA ACACCAAGGT GGACAAGAAA GTTGAGCCCA
       TGGGTCTGGA TGTAGACGTT GCACTTAGTG TTCGGGTCGT TGTGGTTCCA CCTGTTCTTT CAACTCGGGT
```

Figure 1A

```
                                  Human G1 Constant Region
          · S  C  D    K  T  H    T  C  P  P    C  P  A    P  E  L    L  G  G  P    S  V  F ·
  701   AATCTTGTGA CAAAACTCAC ACATGCCCAC CGTGCCCAGC ACCTGAACTC CTGGGGGGAC CGTCAGTCTT
        TTAGAACACT GTTTTGAGTG TGTACGGGTG GCACGGGTCG TGGACTTGAG GACCCCCCTG GCAGTCAGAA Human G1 Constant Region
          · L  F  P    P  K  P  K    D  T  L    M  I  S    R  T  P  E    V  T  C    V  V  V
  771   CCTCTTCCCC CCAAAACCCA AGGACACCCT CATGATCTCC CGGACCCCTG AGGTCACATG CGTGGTGGTG
        GGAGAAGGGG GGTTTTGGGT TCCTGTGGGA GTACTAGAGG GCCTGGGGAC TCCAGTGTAC GCACCACCAC Human G1 Constant Region
           D  V  S  H    E  D  P    E  V  K    F  N  W  Y    V  D  G    V  E  V    H  N  A  K ·
  841   GACGTGAGCC ACGAAGACCC TGAGGTCAAG TTCAACTGGT ACGTGGACGG CGTGGAGGTG CATAATGCCA
        CTGCACTCGG TGCTTCTGGG ACTCCAGTTC AAGTTGACCA TGCACCTGCC GCACCTCCAC GTATTACGGT Human G1 Constant Region
          · T  K  P    R  E  E    Q  Y  N  S    T  Y  R    V  V  S    V  L  T  V    L  H  Q ·
  911   AGACAAAGCC GCGGGAGGAG CAGTACAACA GCACGTACCG TGTGGTCAGC GTCCTCACCG TCCTGCACCA
        TCTGTTTCGG CGCCCTCCTC GTCATGTTGT CGTGCATGGC ACACCAGTCG CAGGAGTGGC AGGACGTGGT Human G1 Constant Region
          · D  W  L    N  G  K  E    Y  K  C    K  V  S    N  K  A  L    P  A  P    I  E  K
  981   GGACTGGCTG AATGGCAAGG AGTACAAGTG CAAGGTCTCC AACAAAGCCC TCCCAGCCCC CATCGAGAAA
        CCTGACCGAC TTACCGTTCC TCATGTTCAC GTTCCAGAGG TTGTTTCGGG AGGGTCGGGG GTAGCTCTTT Human G1 Constant Region
           T  I  S  K    A  K  G    Q  P  R    E  P  Q  V    Y  T  L    P  P  S    R  E  E  M ·
 1051   ACCATCTCCA AAGCCAAAGG GCAGCCCCGA GAACCACAGG TGTACACCCT GCCCCCATCC CGGGAAGAGA
        TGGTAGAGGT TTCGGTTTCC CGTCGGGGCT CTTGGTGTCC ACATGTGGGA CGGGGGTAGG GCCCTTCTCT Human G1 Constant Region
          · T  K  N    Q  V  S    L  T  C  L    V  K  G    F  Y  P    S  D  I  A    V  E  W ·
 1121   TGACCAAGAA CCAGGTCAGC CTGACCTGCC TGGTCAAAGG CTTCTATCCC AGCGACATCG CCGTGGAGTG
        ACTGGTTCTT GGTCCAGTCG GACTGGACGG ACCAGTTTCC GAAGATAGGG TCGCTGTAGC GGCACCTCAC Human G1 Constant Region
          · E  S  N    G  Q  P  E    N  N  Y    K  T  T    P  P  V  L    D  S  D    G  S  F
 1191   GGAGAGCAAT GGGCAGCCGG AGAACAACTA CAAGACCACG CCTCCCGTGC TGGACTCCGA CGGCTCCTTC
        CCTCTCGTTA CCCGTCGGCC TCTTGTTGAT GTTCTGGTGC GGAGGGCACG ACCTGAGGCT GCCGAGGAAG Human G1 Constant Region
           F  L  Y  S    K  L  T    V  D  K    S  R  W  Q    Q  G  N    V  F  S    C  S  V  M ·
 1261   TTCCTCTACA GCAAGCTCAC CGTGGACAAG AGCAGGTGGC AGCAGGGGAA CGTCTTCTCA TGCTCCGTGA
        AAGGAGATGT CGTTCGAGTG GCACCTGTTC TCGTCCACCG TCGTCCCCTT GCAGAAGAGT ACGAGGCACT Human G1 Constant Region
          · H  E  A    L  H  N    H  Y  T  Q    K  S  L    S  L  S    P  G  K  *
 1331   TGCATGAGGC TCTGCACAAC CACTACACGC AGAAGAGCCT CTCCCTGTCT CCGGGTAAAT GA
        ACGTACTCCG AGACGTGTTG GTGATGTGCG TCTTCTCGGA GAGGGACAGA GGCCCATTTA CT
```

Figure 1B

```
                                                                                    Variable Region
                                    Leader Sequence
         M   G   W   S   C   I  I   L   F   L    V   A   T   A   T   G   V   H   S   D    I   Q   M   T ·
   1     ATGGGATGGT CATGTATCAT CCTTTTTCTA GTAGCAACTG CAACCGGTGT ACATTCAGAT ATCCAGATGA
         TACCCTACCA GTACATAGTA GGAAAAAGAT CATCGTTGAC GTTGGCCACA TGTAAGTCTA TAGGTCTACT
                                    Variable Region
         · Q   S   P   S   S   L    S   A   S   V   G   D   R    V   T   I   T   C   R   S    S   Q   S ·
   71    CCCAGTCCCC GAGCTCCCTG TCCGCCTCTG TGGGCGATAG GGTCACCATC ACCTGCAGAT CCAGTCAAAG
         GGGTCAGGGG CTCGAGGGAC AGGCGGAGAC ACCCGCTATC CCAGTGGTAG TGGACGTCTA GGTCAGTTTC
                                    Variable Region
         · L   V   H   S   N   G   N   T   F   L   H   W   Y   Q   Q   K   P    G   K   A   P   K   L
   141   CTTAGTACAT AGCAATGGTA ACACTTTCCT CCACTGGTAT CAACAGAAAC CAGGAAAAGC TCCGAAACTA
         GAATCATGTA TCGTTACCAT TGTGAAAGGA GGTGACCATA GTTGTCTTTG GTCCTTTTCG AGGCTTTGAT
                                    Variable Region
         L    I   Y   T   V   S   N   R   F   S    G   V   P   S   R   F   S    G   S   G   S   G   T   D ·
   211   CTGATTTACA CTGTTAGCAA CCGGTTCTCT GGAGTCCCTT CTCGCTTCTC TGGATCCGGT TCTGGGACGG
         GACTAAATGT GACAATCGTT GGCCAAGAGA CCTCAGGGAA GAGCGAAGAG ACCTAGGCCA AGACCCTGCC
                                    Variable Region
         · F   T   L   T   I   S    S   L   Q   P    E   D   F    A   T   Y   F   C   S    Q   T   T   H ·
   281   ATTTCACTCT GACCATCAGC AGTCTGCAGC CAGAAGACTT CGCTACGTAT TTCTGTAGTC AGACTACTCA
         TAAAGTGAGA CTGGTAGTCG TCAGACGTCG GTCTTCTGAA GCGATGCATA AAGACATCAG TCTGATGAGT
                                                                                Human Kappa Constant Region
                                    Variable Region
         · V   P   W   T   F   G    Q   G   T   K    V   E   I    K   R   T   V   A   A   P   S   V   F
   351   TGTTCCATGG ACATTTGGAC AGGGTACCAA GGTGGAGATC AAACGAACTG TGGCTGCACC ATCTGTCTTC
         ACAAGGTACC TGTAAACCTG TCCCATGGTT CCACCTCTAG TTTGCTTGAC ACCGACGTGG TAGACAGAAG
                                Human Kappa Constant Region
         I . P   P   S    D   E   Q   L   K    S   G   T   A   S    V   V   C   L   L   N   N   F   Y ·
   421   ATCTTCCCGC CATCTGATGA GCAGTTGAAA TCTGGAACTG CTTCTGTTGT GTGCCTGCTG AATAACTTCT
         TAGAAGGGCG GTAGACTACT CGTCAACTTT AGACCTTGAC GAAGACAACA CACGGACGAC TTATTGAAGA
                                Human Kappa Constant Region
         · P   R   E   A   K   V    Q   W   K   V    D   N   A   L   Q   S   G   N   S   Q   E   S   V ·
   491   ATCCCAGAGA GGCCAAAGTA CAGTGGAAGG TGGATAACGC CCTCCAATCG GGTAACTCCC AGGAGAGTGT
         TAGGGTCTCT CCGGTTTCAT GTCACCTTCC ACCTATTGCG GGAGGTTAGC CCATTGAGGG TCCTCTCACA
                                Human Kappa Constant Region
         · T   E   Q   D   S   K    D   S   T   Y    S   L   S   S   T   L   T   L   S   K   A   D   Y
   561   CACAGAGCAG GACAGCAAGG ACAGCACCTA CAGCCTCAGC AGCACCCTGA CGCTGAGCAA AGCAGACTAC
         GTGTCTCGTC CTGTCGTTCC TGTCGTGGAT GTCGGAGTCG TCGTGGGACT GCGACTCGTT TCGTCTGATG
                                Human Kappa Constant Region
         E   K   H   K   V   Y   A   C   E   V    T   H   Q   G   L   S   S    P   V   T    K   S   F   N ·
   631   GAGAAACACA AAGTCTACGC CTGCGAAGTC ACCCATCAGG GCCTGAGCTC GCCCGTCACA AAGAGCTTCA
         CTCTTTGTGT TTCAGATGCG GACGCTTCAG TGGGTAGTCC CGGACTCGAG CGGGCAGTGT TTCTCGAAGT
         Human Kappa Constant Region

· R   G   E   C   *
   701   ACAGGGGAGA GTGTTAA
         TGTCCCCTCT CACAATT
```

Figure 1C

SEQUENCE LISTING

```
<160> NUMBER OF SEQ ID NOS: 22

<210> SEQ ID NO 1
<211> LENGTH: 113
<212> TYPE: PRT
<213> ORGANISM: MusMusculus

<400> SEQUENCE: 1

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Ser His Gly Lys Ser Leu Glu Trp Ile
        35                  40                  45

Gly Arg Val Ile Pro Asn Asn Gly Gly Thr Ser Tyr Asn Gln Lys Phe
    50                  55                  60
```

```
Lys Gly Lys Ala Ile Leu Thr Val Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Gly Ile Tyr Trp Trp Gly His Gly Thr Thr Leu Thr Val
            100                 105                 110

Ser

<210> SEQ ID NO 2
<211> LENGTH: 116
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Val Ile Ser Gly Asp Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Gly Gly Ser Asp Tyr Trp Gly Gln Gly Thr Leu
            100                 105                 110

Val Thr Val Ser
        115

<210> SEQ ID NO 3
<211> LENGTH: 113
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
 1               5                  10                  15

Ser Leu Arg Leu Ser Cys Ala Ser Gly Tyr Ser Phe Thr Gly Tyr
                20                  25                  30

Tyr Ile His Trp Val Arg Gln Ala Pro Gly Lys Gly Leu Glu Trp Val
            35                  40                  45

Ala Arg Val Ile Pro Asn Asn Gly Gly Thr Ser Tyr Asn Gln Lys Phe
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Leu Val Thr Val
            100                 105                 110

Ser
```

```
<210> SEQ ID NO 4
<211> LENGTH: 113
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Asn Gly Gly Thr Ser Tyr Asn Gln Lys Phe
    50                  55                  60

Lys Gly Arg Phe Thr Ile Ser Val Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser

<210> SEQ ID NO 5
<211> LENGTH: 113
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Asn Gly Gly Thr Ser Tyr Asn Gln Lys Phe
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser

<210> SEQ ID NO 6
<211> LENGTH: 113
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30
```

```
Tyr Ile His Trp Val Arg Gln Ala Pro Gly Lys Gly Leu Glu Trp Val
            35                  40                  45

Ala Arg Val Ile Pro Asn Asn Gly Gly Thr Ser Tyr Asn Gln Lys Phe
 50                  55                  60

Lys Gly Arg Ala Thr Leu Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
                100                 105                 110

Ser

<210> SEQ ID NO 7
<211> LENGTH: 113
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Tyr Ile His Trp Val Arg Gln Ala Pro Gly Lys Gly Leu Glu Trp Val
            35                  40                  45

Ala Arg Val Ile Pro Asn Asn Gly Gly Thr Ser Tyr Asn Gln Lys Phe
 50                  55                  60

Lys Gly Arg Phe Thr Leu Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
                100                 105                 110

Ser

<210> SEQ ID NO 8
<211> LENGTH: 113
<212> TYPE: PRT
<213> ORGANISM: Artificial
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Tyr Ile His Trp Val Arg Gln Ala Pro Gly Lys Gly Leu Glu Trp Val
            35                  40                  45

Ala Arg Val Ile Pro Asn Asn Gly Gly Thr Ser Tyr Asn Gln Lys Phe
 50                  55                  60

Lys Gly Arg Ala Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                85                  90                  95
```

-continued

Ala Arg Glu Gly Ile Tyr Trp Trp Gly Gln Gly Thr Leu Val Thr Val
            100                 105                 110

Ser

<210> SEQ ID NO 9
<211> LENGTH: 113
<212> TYPE: PRT
<213> ORGANISM: Artificial
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Asn Gly Gly Thr Ser Tyr Asn Gln Lys Phe
    50                  55                  60

Lys Gly Arg Ala Thr Leu Ser Val Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser

<210> SEQ ID NO 10
<211> LENGTH: 113
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Ala Gly Gly Thr Ser Tyr Asn Gln Lys Phe
    50                  55                  60

Lys Gly Arg Phe Thr Leu Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser

<210> SEQ ID NO 11
<211> LENGTH: 113
<212> TYPE: PRT
<213> ORGANISM: Artificial
<220> FEATURE:
<223> OTHER INFORMATION: Synthetic Construct -continued

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Gln Gly Gly Thr Ser Tyr Asn Gln Lys Phe
    50                  55                  60

Lys Gly Arg Phe Thr Leu Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser

<210> SEQ ID NO 12
<211> LENGTH: 113
<212> TYPE: PRT
<213> ORGANISM: MusMusculus

<400> SEQUENCE: 12

Asp Val Val Val Thr Gln Thr Pro Leu Ser Leu Pro Val Ser Leu Gly
1               5                   10                  15

Ala Gln Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Trp Thr Phe Gly Gly Gly Thr Lys Leu Glu Ile Gln
            100                 105                 110

Arg

<210> SEQ ID NO 13
<211> LENGTH: 108
<212> TYPE: PRT
<213> ORGANISM: Artificial
<220> FEATURE:
<223> OTHER INFORMATION: Synthetic Construct

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Asn Ser Leu Pro Trp
                85                  90                  95

Thr Phe Gly Gly Gly Thr Lys Leu Glu Ile Gln Arg
            100                 105
```

<210> SEQ ID NO 14
<211> LENGTH: 113
<212> TYPE: PRT
<213> ORGANISM: Artificial
<220> FEATURE:
<223> OTHER INFORMATION: Synthetic Construct

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Thr
                85                  90                  95

Thr His Val Pro Trp Thr Phe Gly Gln Gly Thr Lys Val Glu Ile Lys
            100                 105                 110

Arg
```

<210> SEQ ID NO 15
<211> LENGTH: 113
<212> TYPE: PRT
<213> ORGANISM: Artificial
<220> FEATURE:
<223> OTHER INFORMATION: Synthetic Construct

<400> SEQUENCE: 15

```
Asp Val Gln Val Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Thr
                85                  90                  95

Thr His Val Pro Trp Thr Phe Gly Gln Gly Thr Lys Val Glu Ile Lys
            100                 105                 110

Arg
```

<210> SEQ ID NO 16
<211> LENGTH: 113
<212> TYPE: PRT
<213> ORGANISM: Artificial
<220> FEATURE:
<223> OTHER INFORMATION: Synthetic Construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gln Gly Thr Lys Val Glu Ile Lys
            100                 105                 110

Arg

<210> SEQ ID NO 17
<211> LENGTH: 1392
<212> TYPE: DNA
<213> ORGANISM: Artificial Sequence
<220> FEATURE:
<223> OTHER INFORMATION: Synthetic Construct

<400> SEQUENCE: 17

| | | | | | |
|---|---|---|---|---|---|
| atgggatggt | catgtatcat | ccttttttcta | gtagcaactg | caactggagt | acattcagaa | 60 |
| gttcagctgg | tggagtctgg | cggtggcctg | gtgcagccag | ggggctcact | ccgtttgtcc | 120 |
| tgtgcagctt | ctggctacag | cttcaccggt | tattacatcc | actgggtccg | tcaggccccg | 180 |
| ggtaagggcc | tggaatgggt | tgcaagggtt | attcctaacg | ccggcggtac | cagttataac | 240 |
| cagaagttca | agggccgttt | cacattgagc | gtcgacaatt | ccaaaaacac | agcatacctg | 300 |
| cagatgaaca | gcctgcgtgc | tgaggacact | gccgtctatt | attgtgctcg | agagggtatc | 360 |
| tactggtggg | gtcaaggaac | cctggtcacc | gtctcctcgg | cctccaccaa | gggcccatcg | 420 |
| gtcttccccc | tggcaccctc | ctccaagagc | acctctgggg | gcacagcggc | cctgggctgc | 480 |
| ctggtcaagg | actacttccc | cgaaccggtg | acggtgtcgt | ggaactcagg | cgccctgacc | 540 |
| agcggcgtgc | acaccttccc | ggctgtccta | cagtcctcag | gactctactc | cctcagcagc | 600 |
| gtggtgactg | tgccctctag | cagcttgggc | acccagacct | acatctgcaa | cgtgaatcac | 660 |
| aagcccagca | acaccaaggt | ggacaagaaa | gttgagccca | atcttgtgac | aaaaactcac | 720 |
| acatgcccac | cgtgcccagc | acctgaactc | ctggggggac | cgtcagtctt | cctcttcccc | 780 |
| ccaaaaccca | aggacaccct | catgatctcc | cggacccctg | aggtcacatg | cgtggtggtg | 840 |
| gacgtgagcc | acgaagaccc | tgaggtcaag | ttcaactggt | acgtggacgg | cgtggaggtg | 900 |
| cataatgcca | agacaaagcc | gcgggaggag | cagtacaaca | gcacgtaccg | tgtggtcagc | 960 |
| gtcctcaccg | tcctgcacca | ggactggctg | aatggcaagg | agtacaagtg | caaggtctcc | 1020 |
| aacaaagccc | tcccagcccc | catcgagaaa | accatctcca | aagccaaagg | gcagccccga | 1080 |
| gaaccacagg | tgtacaccct | gcccccatcc | cgggaagaga | tgaccaagaa | ccaggtcagc | 1140 |
| ctgacctgcc | tggtcaaagg | cttctatccc | agcgacatcg | ccgtggagtg | ggagagcaat | 1200 |
| gggcagccgg | agaacaacta | caagaccacg | cctcccgtgc | tggactccga | cggctccttc | 1260 |
| ttcctctaca | gcaagctcac | cgtggacaag | agcaggtggc | agcaggggaa | cgtcttctca | 1320 |

```
tgctccgtga tgcatgaggc tctgcacaac cactacacgc agaagagcct ctccctgtct    1380
ccgggtaaat ga                                                        1392
```

<210> SEQ ID NO 18
<211> LENGTH: 463
<212> TYPE: PRT
<213> ORGANISM: Artificial Sequence
<220> FEATURE:
<223> OTHER INFORMATION: Synthetic Construct

<400> SEQUENCE: 18

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Ser Phe
        35                  40                  45

Thr Gly Tyr Tyr Ile His Trp Val Arg Gln Ala Pro Gly Lys Gly Leu
    50                  55                  60

Glu Trp Val Ala Arg Val Ile Pro Asn Ala Gly Gly Thr Ser Tyr Asn
65                  70                  75                  80

Gln Lys Phe Lys Gly Arg Phe Thr Leu Ser Val Asp Asn Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Glu Gly Ile Tyr Trp Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350
```

```
Ser Lys Ala Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 19
<211> LENGTH: 444
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Ala Gly Gly Thr Ser Tyr Asn Gln Lys Phe
    50                  55                  60

Lys Gly Arg Phe Thr Leu Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Glu Gly Ile Tyr Trp Trp Gly Gln Gly Thr Leu Val Thr Val
        100                 105                 110

Ser Ser Ala Ser Thr Lys Gly Pro Ser Val Phe Pro Leu Ala Pro Ser
    115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
        180                 185                 190

Gln Thr Tyr Ile Cys Asn Val Asn His Lys Pro Ser Asn Thr Lys Val
    195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255
```

```
Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 20
<211> LENGTH: 717
<212> TYPE: DNA
<213> ORGANISM: Artificial
<220> FEATURE:
<223> OTHER INFORMATION: Synthetic Construct

<400> SEQUENCE: 20
atgggatggt catgtatcat ccttttttcta gtagcaactg caaccggtgt acattcagat      60
atccagatga cccagtcccc gagctccctg tccgcctctg tgggcgatag ggtcaccatc     120
acctgcagat ccagtcaaag cttagtacat agcaatggta cactttttcct ccactggtat    180 caacagaaac aggaaaaagc tccgaaacta ctgatttaca ctgttagcaa ccggttctct     240
ggagtccctt ctcgcttctc tggatccggt tctgggacgg atttcactct gaccatcagc    300
agtctgcagc cagaagactt cgctacgtat ttctgtagtc agactactca tgttccatgg   360
acatttggac agggtaccaa ggtggagatc aaacgaactg tggctgcacc atctgtcttc   420
atcttcccgc catctgatga gcagttgaaa tctggaactg cttctgttgt gtgcctgctg   480 ataacttct atcccagaga ggccaaagta cagtggaagg tggataacgc cctccaatcg    540
ggtaactccc aggagagtgt cacagagcag gacagcaagg acagcaccta cagcctcagc   600
agcaccctga cgctgagcaa agcagactac gagaaacaca agtctacgc ctgcgaagtc    660 acccatcagg gcctgagctc gcccgtcaca aagagcttca caggggagag tgttaa       717

<210> SEQ ID NO 21
<211> LENGTH: 238
<212> TYPE: PRT
<213> ORGANISM: Artificial Sequence
<220> FEATURE:
<223> OTHER INFORMATION: Synthetic Construct
```

-continued

<400> SEQUENCE: 21

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ser Ser Gln Ser Leu
        35                  40                  45

Val His Ser Asn Gly Asn Thr Phe Leu His Trp Tyr Gln Gln Lys Pro
    50                  55                  60

Gly Lys Ala Pro Lys Leu Leu Ile Tyr Thr Val Ser Asn Arg Phe Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Ser Gln Thr Thr His Val Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 22
<211> LENGTH: 219
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

-continued

```
Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155                 160

Ser Gly Asn Ser Gln Glu Ser Val Thr Glu Gln Asp Ser Lys Asp Ser
                165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215
```

HUMANIZED ANTI-CD40 ANTIBODIES AND THEIR METHODS OF USE

CONTINUITY

This application is a 35 U.S.C. 371 National Stage of International Application No. PCT/US2006/020688, filed May 26, 2006. PCT/US2006/020688 claims the benefit of U.S. Provisional Application No. 60/684,853, filed May 26, 2005, the disclosure of which is incorporated by reference herein in its entirety for all purposes.

This application claims the benefit of U.S. Provisional Application No. 60/684,853, filed May 26, 2005; the disclosure of which is incorporated by reference herein in its entirety.

BACKGROUND

This invention generally relates to humanized anti-CD40 antibodies for diagnostic and therapeutic use. More specifically, humanized anti-CD40 antibodies and methods of use for the treatment of various diseases or disorders characterized by cells expressing CD40 are disclosed. Pharmaceutical compositions and articles of manufacture such as kits comprising the humanized anti-CD40 antibody are also disclosed.

CD40 is a type I integral membrane glycoprotein and a member of the tumor necrosis factor (TNF) receptor superfamily. CD40 is expressed on a variety of cell types including normal and neoplastic B cells, interdigitating cells, basal epithelial cells and carcinomas. It is also present on monocytes, macrophages, some endothelial cells, and follicular dendritic cells. CD40 is expressed early in B cell ontogeny, appearing on B cell precursors subsequent to the appearance of CD10 and CD19, but prior to expression of CD21, CD23, CD24, and appearance of surface immunoglobulin M (sIgM) (Uckun et al., 1990, *Blood* 15:2449). Although early reports indicated that CD40 was lost upon terminal differentiation of B cells into plasma cells, CD40 has been detected on tonsil and bone marrow-derived plasma cells (Pellat-Decounynck et al., 1994, *Blood* 84:2597).

The interaction of CD40 with its ligand and counter-receptor, CD40L (also referred to as CD154, gp39, and TRAP), induces both humoral and cell-mediated immune responses. CD40L is a transmembrane protein expressed predominantly on activated lymphocytes.CD4+ T cells. Like other proteins in the TNF family, the structure of CD40L is that of a noncovalent trimer. CD40-mediated signaling appears to be required for B cell proliferation, immunoglobulin (Ig) isotype switching, germinal center formulation, and memory B cell commitment in response to T cell-dependent antigen. CD40 binding of CD40L results in CD40 multimerization, the generation of activation signals for antigen presenting cells such as dendritic cells, monocytes, and B cells, and the generation of growth and differentiation signals for cytokine-activated fibroblasts and epithelial cells. While the signaling pathways through which CD40 molecules function in cell differentiation have not been completely elucidated, CD40 signals are transduced from the multimerized receptor via recruitment of a series of TNF receptor associated factors ("TRAFs") (Kehry, 1996, *J. Immumol.* 156:2345-2348). Subsets of TRAFs interact differentially with TNF receptor family members, including CD40, providing stimuli to a wide variety of downstream pathways. TRAF1 and TRAF2 are implicated in the modulation of apoptosis (Speiser et al., 1997, *J. Exp. Med.* 185:1777-1783; Yeh et al., 1997, *Immunity* 7:715-725). TRAFs 2, 5, and 6 participate in proliferation and activation events. In normal B cells, binding of CD40 to CD40L recruits TRAF2 and TRAF3 to the receptor complex and induces down regulation of other TRAF's (Kuhne et al., 1997, *J. Exp. Med.* 186:337-342).

Apoptosis and CD40-mediated signaling are closely linked during B cell development and differentiation. A primary function of apoptosis in B cells is the clonal deletion of immature B cells, which is thought to result from extensive cross-linking of surface Ig in immature B cells. The fate of mature B cells is also modulated by a combination of signaling via surface Ig and signals derived form activated T cells, presumably mediated by CD40L molecules. A combination of signals from surface Ig and CD40 can override the apoptotic pathway and maintain germinal center B cell survival. This rescue from apoptosis in germinal centers is critical for the development of affinity antibody-producing memory B cells.

In both T and B cell malignancies, antitumor effects (growth arrest with or without apoptosis) often result when malignant cells are exposed to stimuli that lead to activation of normal lymphocytes. This activation-induced growth arrest has been observed with signals through either antigen receptors or costimulatory receptors (Ashwell et al., 1987, *Science* 237:61; Bridges et al., 1987, *J. Immumol.* 139:4242; Page and Defranco, 1988 *J. Immunol.* 140:3717; and Beckwith et al., 1990, *J. Natl. Cancer Inst.* 82:501). CD40 stimulation by either anti-CD40 antibody or soluble CD40L directly inhibits B cell lymphoma growth (Funakoshi et al., 1994, *Blood* 83:2787-2784).

Several murine monoclonal antibodies (mAbs) directed against CD40 have been described (Katira et al. 1995, "CD40 Workshop Panel Report"; In: *Leukocyte Typing V*, Schlossman et al., (eds) 1995, 1:547-550). For example, two mAbs, CD40.7 (M2) and CD40.8 (M3), were shown to inhibit the binding of CD40 to CD40L (Fanslow et al., 1995, In: *Leukocyte Typing V*, Schlossman et al., (eds) 1995, 1:555-556). CD40 stimulation by mAbs M2 and M3 inhibited growth of several human B-cell lymphomas and induced regression of established tumors in vivo (Funakoshi et al., 1994, *Blood* 83:2787-2794; Funakoshi et al., 1996, *J. Immunol.* 19:93-101). U.S. Pat. No. 5,182,368 discloses an anti-CD40 murine mAb, G28-5, which can augment B cell proliferation. A single chain immunotoxin based the single-chain Fv region of G28-5 selectively killed human CD40-expressing hematologic malignant cell lines in vitro (Francisco et al., 1997, *J. Biol. Chem.* 39:24165-24169). However, G28-5 does not enhance activation of B cells in the presence of CD40L and does not potentiate the binding of CD40 and CD40L. U.S. Pat. No. 6,838,261 (and related U.S. Pat. Nos. 6,946,129 and 6,843,989) describes a class of variant forms of the anti-CD40 murine mAb, S2C6, and its use in the treatment of various disorders, including cancer and immunological and inflammatory diseases. In addition to enhancing CD40L-mediated stimulation, an anti-CD40 antibody described in U.S. Pat. No. 6,838,261 showed enhancement of the interaction between CD40 and CD40L, and in vivo anti-neoplastic activity. Although S2C6 by itself will stimulate B cell proliferation in a manner similar to G28-5, S2C6 is distinguished from G28-5 by its ability to increase CD40L binding and the subsequent magnitude of the CD40L-mediated activation signal.

Other murine anti-CD40 mAbs, e.g., described in International Publication Number WO 95/17202, bind CD40 and show efficacy in the treatment and prevention of disease characterized by neoplastic cells expressing CD40. Although murine anti-CD40 antibodies have potential applicability as therapeutic agents in the treatment of CD40-related diseases in humans, their immunogenicity presents the possibility of a neutralizing antibody response, e.g., a human anti-mouse antibody (HAMA) response which would limit their value.

Thus, there is a need for humanized anti-CD40 antibodies that specifically bind defined CD40 epitopes and which show the antigen binding specificity, affinity, and other desired functional characteristics of the analogous nonhuman anti-CD40 antibody.

BRIEF SUMMARY

The present invention encompasses humanized anti-CD40 antibodies and antigen binding fragments thereof, as well as methods using such humanized anti-CD40 antibodies and fragments for the treatment of diseases and disorders characterized by cells expressing the CD40 surface antigen. Also included are kits and articles of manufacture comprising a humanized anti-CD40 antibody.

In some embodiments, an isolated antibody or antigen-binding fragment that specifically binds to human CD40 is provided. The antibody or antigen-binding fragment includes a heavy chain variable domain and/or light chain variable region domain. The heavy chain variable region domain can include a framework region having an amino acid sequence at least 90% identical to the amino acid sequence of the human variable domain heavy chain subgroup III consensus amino acid sequence of SEQ ID NO:2, and at least one CDR having an amino acid sequence at least 90% identical to a corresponding heavy chain CDR of SEQ ID NO:3. The light chain variable domain can include a framework region having an amino acid sequence at least 90% identical to the human variable domain light chain subgroup kappa I consensus amino acid sequence of SEQ ID NO: 13, and at least one CDR having an amino acid sequence at least 90% identical to a corresponding light chain CDR of SEQ ID NO:14.

In some embodiments, each heavy chain CDR is at least 90% identical to the corresponding heavy chain CDR of SEQ ID NO:3. In some embodiments, the heavy chain CDRs include the amino acid sequences of the heavy chain CDR1, CDR2 and CDR3 of SEQ ID NO:3. In some embodiments, each light chain CDR is at least 90% identical to the corresponding light chain CDR of SEQ ID NO:14. In some embodiments, the light chain CDRs include the amino acid sequences of the CDR1, CDR2 and CDR3 of SEQ ID NO:14.

In some embodiments, the antibody or antigen-binding fragment includes a heavy chain variable domain having the amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO: 10, or SEQ ID NO:11. In some embodiments, the antibody or antigen-binding fragment includes a light chain variable domain having the amino acid sequence of SEQ ID NO:14, SEQ ID NO:15, or SEQ ID NO:16. In some embodiments, the antibody or antigen-binding fragment has the heavy chain variable domain amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and the light chain variable domain amino acid sequence of SEQ ID NO: 14, SEQ ID NO: 15, or SEQ ID NO: 16.

In some embodiments, the heavy chain variable domain and the light chain variable domain include the amino acid sequences of SEQ ID NO:3 and SEQ ID NO: 14, respectively; SEQ ID NO:4 and SEQ ID NO:14, respectively; SEQ ID NO:5 and SEQ ID NO:14, respectively; SEQ ID NO:6 and SEQ ID NO:14, respectively; SEQ ID NO:7 and SEQ ID NO: 14, respectively; SEQ ID NO:8 and SEQ ID NO: 14, respectively; SEQ ID NO:9 and SEQ ID NO:14, respectively; SEQ ID NO:6 and SEQ ID NO:15, respectively; SEQ ID NO:6 and SEQ ID NO:16, respectively; SEQ ID NO:7 and SEQ ID NO:16, respectively; SEQ ID NO: 10 and SEQ ID NO: 14, respectively; SEQ ID NO:11 and SEQ ID NO:14, respectively; SEQ ID NO:10 and SEQ ID NO:16, respectively; or SEQ ID NO:11 and SEQ ID NO: 16, respectively.

The antibody or antigen-binding fragment can include a human IgG constant region, such as, for example, an IgG constant region of isotype IgG1, IgG2, IgG3, or IgG4. The antibody or antigen-binding fragment can include a light chain constant domain, such as, for example, a kappa constant domain.

In some embodiments, the antibody is hu sgn-0, hu sgn-1, hu sgn-2, hu sgn-4, hu sgn-14, hu sgn-15, hu sgn-16, hu sgn-17, hu sgn-18, hu sgn-19, hu sgn-22, hu sgn-23, hu sgn-26 or hu sgn-27. In some embodiments, the antibody or antigen-binding fragment competes for binding with monoclonal antibody S2C6 that is secreted by a hybridoma having ATCC Accession No. PTA-110.

The antibody also can be an antigen-binding fragment, such as a Fab, a Fab', a F(ab')2, a Fv fragment, a diabody, a single-chain antibody, an scFv fragment or an scFv-Fc. The antibody or antigen-binding fragment can optionally be labeled or conjugated to a chemotherapeutic agent, such as an auristatin (e.g., MMAE or MMAF).

Also provided is a kit including an anti-CD40 antibody or antigen binding fragment in a container. The kit can optionally include an additional component(s), such as instructions for using the antibody to detect CD40 protein in a biological sample.

Pharmaceutical compositions comprising an anti-CD40 antibody or antigen-binding fragment thereof and a pharmaceutically acceptable excipients(s) are also provided.

In some embodiments, isolated polynucleotides encoding a humanized heavy chain variable region and/or a humanized light chain variable region are provided. A polynucleotide can, for example, encode the heavy chain variable domain amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. A polynucleotide also can, for example, encode the light chain variable domain amino acid sequence of SEQ ID NO:14, SEQ ID NO:15, or SEQ ID NO:16.

In some embodiments, isolated polynucleotide encodes the heavy chain variable domain amino acid sequence and the light chain variable domain amino acid sequence of SEQ ID NO:3 and SEQ ID NO: 14, respectively; SEQ ID NO:4 and SEQ ID NO:14, respectively; SEQ ID NO:5 and SEQ ID NO:14, respectively; SEQ ID NO:6 and SEQ ID NO:14, respectively; SEQ ID NO:7 and SEQ ID NO:14, respectively; SEQ ID NO:8 and SEQ ID NO:14, respectively; SEQ ID NO:9 and SEQ ID NO:14, respectively; SEQ ID NO:6 and SEQ ID NO:15, respectively; SEQ ID NO:6 and SEQ ID NO:16, respectively; SEQ ID NO:7 and SEQ ID NO:16, respectively; SEQ ID NO:10 and SEQ ID NO: 14, respectively; SEQ ID NO: 11 and SEQ ID NO: 14, respectively; SEQ ID NO:10 and SEQ ID NO:16, respectively; or SEQ ID NO:11 and SEQ ID NO:16, respectively.

In some embodiments, methods for inhibiting the growth of cells expressing human CD40 antigen are provided. The methods include administering an anti-CD40 antibody or an antigen-binding fragment to the cells, which antibody or antigen-binding fragment binds to the human cell surface CD40 antigen. The binding of the antibody or antigen-binding fragment to the CD40 antigen inhibits the growth or differentiation of the cells.

In some embodiments, methods for treating a subject having a CD40-associated disorder are provided. The methods include administering to the subject an anti-CD40 antibody or an antigen-binding fragment, which antibody or antigen-binding fragment binds to human CD40. The binding of the antibody or antigen-binding fragment to CD40 inhibits the growth or differentiation of cells of the CD40-associated disorder. The CD40-associated disorder can be, for example, chronic lymphocytic leukemia, Burkitt's lymphoma, multiple myeloma, a T cell lymphoma, Non-Hodgkin's Lymphoma, Hodgkin's Disease, Waldenstrom's macroglobulinemia or Kaposi's sarcoma.

In some embodiments, methods for inducing depletion of peripheral B cells are provided. The methods include administering to the cells an anti-CD40 antibody or an antigen-binding fragment, which antibody or antigen-binding fragment binds to a human cell surface CD40 antigen. The binding of the antibody or antigen-binding fragment to the CD40 antigen induces depletion of the cells. The peripheral B cells can, for example, exhibit autoimmune reactivity in a subject.

The invention will best be understood by reference to the following detailed description including the preferred embodiments, taken in conjunction with the accompanying drawings and sequence listing. The discussion below is descriptive, illustrative and exemplary and is not to be taken as limiting the scope defined by any of the appended claims.

BRIEF DESCRIPTION OF THE DRAWINGS

FIGS. 1A and 1B show the polypeptide (SEQ ID NO: 18) and the coding (SEQ ID NO:17) and complementary DNA sequences of the heavy chain of a humanized anti-CD40 antibody. The polypeptide sequence is annotated to indicate the position of the leader sequence, the variable region, and the human IgG$_1$ constant region. FIG. 1C shows the polypeptide (SEQ ID NO:21) and the coding (SEQ ID NO:20) and complementary DNA sequences of the light chain of a humanized anti-CD40 antibody. The polypeptide sequence is annotated to indicate the position of the leader sequence, the variable region, and the human kappa constant region.

DETAILED DESCRIPTION

Figure 2:
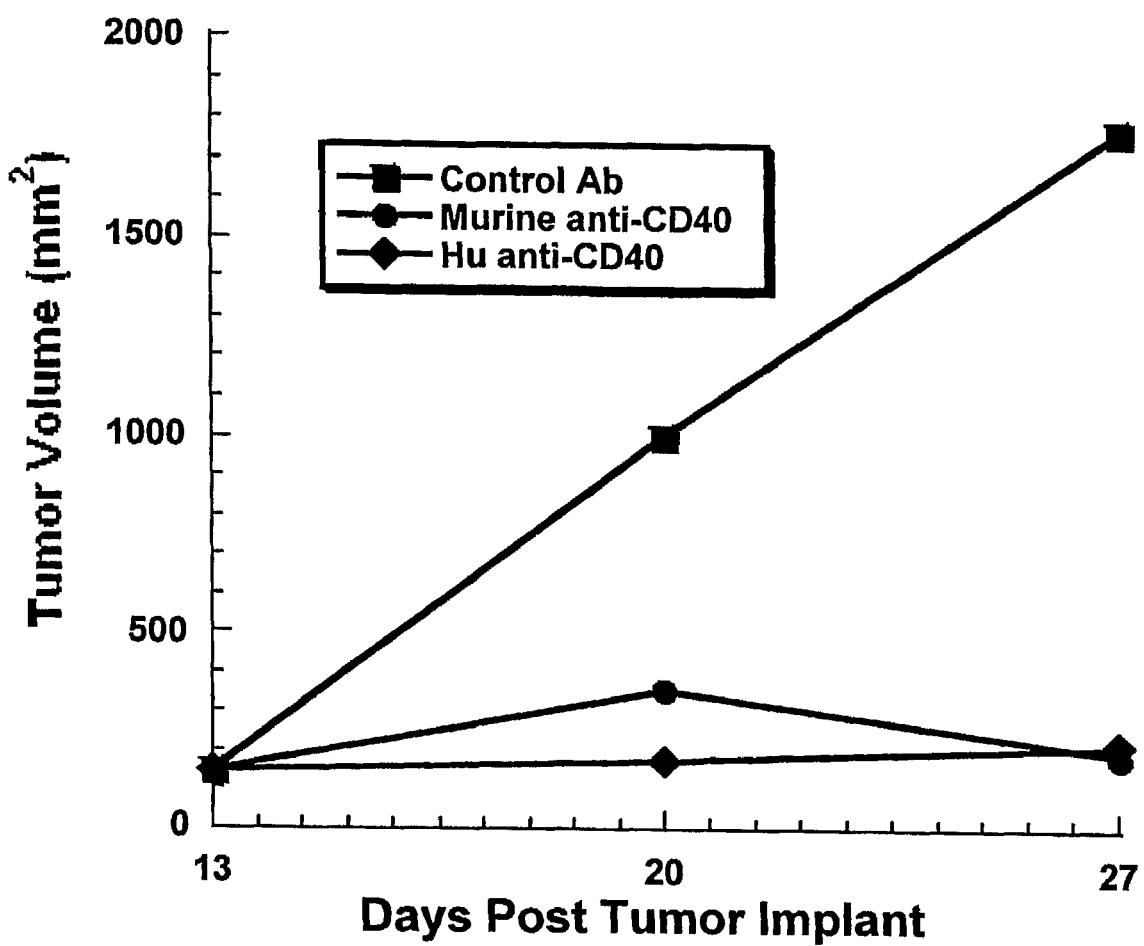
FIG. 2 shows the effect of treatment with a control antibody, a murine anti-CD40 antibody, and a humanized anti-CD40 antibody on tumor volume measured over a two-week period, with treatment beginning 13 days post-tumor tumor transplant.

For clarity of disclosure, and not by way of limitation, the detailed description of the invention is divided into the subsections which follow.

When trade names are used herein, the trade name also refers to the trade name product formulation, the generic drug, and the active pharmaceutical ingredient(s) of the trade name product, unless otherwise indicated by context.

Unless defined otherwise, all technical and scientific terms used herein have the same meaning as commonly understood by one of ordinary skill in the art pertinent to the methods and compositions described.

DEFINITIONS

The terms "CD40" and "CD40 surface antigen" refer to a 50 kD glycoprotein expressed on the surface of normal and neoplastic B cells, which acts as a receptor for signals involved in cellular proliferation and differentiation and is sometimes referred to as Bp50 (Ledbetter et al., 1987, *J. Immunol.* 138:788-785). A cDNA molecule encoding CD40 has been isolated from a library prepared from the Burkitt lymphoma cell line Raji (Stamenkovic et al., 1989, *EMBO J.* 8:1403). A cell that expresses CD40 is any cell characterized by the surface expression of CD40, including, but not limited to, normal and neoplastic B cells, interdigitating cells, basal epithelial cells, carcinoma cells, macrophages, endothelial cells, follicular dendritic cells, tonsil cells, and bone marrow-derived plasma cells. In some embodiments, the CD40 molecule is a human CD40 molecule.

The terms, "CD40 antigen epitope" and "CD40 epitope", as used herein, refer to a molecule (e.g., a peptide) or a fragment of a molecule capable of immunoreactivity with an anti-CD40 antibody and, for example, includes a CD40 antigenic determinant recognized by the S2C6 monoclonal antibody. CD40 antigen epitopes can be included in proteins, protein fragments, peptides or the like. The epitopes are most commonly proteins, short oligopeptides, oligopeptide mimics (i.e., organic compounds that mimic antibody binding properties of the CD40 antigen), or combinations thereof.

As used herein, "specific binding" and "specifically binds" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

"Native antibodies" and "native immunoglobulins" are defined herein as heterotetrameric glycoproteins, typically of about 150,000 daltons, composed of two identical light (L) chain and two identical heavy (H) chains. Each light chain is covalently linked to a heavy chain by one disulfide bond to form a heterodimer. The heterotetramer is formed by covalent disulfide linkage between the two identical heavy chains of such heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain (V$_H$), followed by three or four constant domains (C$_H$1, C$_H$2, C$_H$3, and C$_H$4), as well as a hinge region between C$_H$1 and C$_H$2. Each light chain has two domains, an amino-terminal variable domain (V$_L$) and a carboxy-terminal constant domain (C$_L$). The V$_L$ domain associates non-covalently with the V$_H$ domain, whereas the C$_L$ domain is commonly covalently linked to the C$_H$1 domain via a disulfide bond. Particular amino acid residues are believed to form an interface between the light and heavy chain variable domains (Chothia et al., 1985, *J. Mol. Biol.* 186:651-663.)

The term "hypervariable" refers to the fact that certain sequences within the variable domains differ extensively in sequence among antibodies and contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: *Sequences of Proteins of Immunological Interest*, 5$^{th}$ Ed. Public Health Service, National Institutes of Health, Bethesda, Md., whereas HVLs are structurally defined according to the three-dimensional structure of the variable domain, as described by Chothia and Lesk, 1987, *J. Mol. Biol.* 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains to close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues can have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody dependent cellular cytotoxicity (ADCC), complement dependent cytotoxicity (CDC) and antibody dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-CD40 antibody", "humanized anti-CD40 antibody", and "variant humanized anti-CD40 antibody" are used herein in the broadest sense and specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., CD40 binding.

The term "monoclonal antibody" (mAb) refers to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Köhler et al., 1975, *Nature* 256:495, or recombinant DNA methods known in the art (see, e.g., U.S. Pat. No. 4,816,567). In another example, monoclonal antibodies can also be isolated from phage antibody libraries, using techniques described in Clackson et al., 1991, *Nature* 352: 624-628, and Marks et al., 1991, *J. Mol. Biol.* 222: 581-597.

In contrast, the antibodies in a preparation of polyclonal antibodies are typically a heterogeneous population of immunoglobulin isotypes and/or classes and also exhibit a variety of epitope specificity.

The term "chimeric" antibody as used herein is a type of monoclonal antibody in which a portion of or the complete amino acid sequence in one or more regions or domains of the heavy and/or light chain is identical with, homologous to, or a variant of the corresponding sequence in a monoclonal antibody from another species or belonging to another immunoglobulin class or isotype, or from a consensus sequence. Chimeric antibodies include fragments of such antibodies, provided that the antibody fragment exhibits the desired biological activity of its parent antibody, for example binding to the same epitope (see, e.g., U.S. Pat. No. 4,816,567; and Morrison et al., 1984, *Proc. Natl. Acad. Sci. USA* 81: 6851-6855).

The terms, "antibody fragment", "anti-CD40 antibody fragment", "humanized anti-CD40 antibody fragment", "variant humanized anti-CD40 antibody fragment" refer to a portion of a full length anti-CD40 antibody, in which a variable region or a functional capability is retained, for example, specific CD40 epitope binding. Examples of antibody fragments include, but are not limited to, a Fab, Fab', $F(ab')_2$, Fd, Fv, scFv and scFv-Fc fragment, a diabody, a linear antibody, a single-chain antibody, a minibody, a diabody formed from antibody fragments, and multispecific antibodies formed from antibody fragments.

Certain types of antibody fragments can be generated by enzymatic treatment of a full-length antibody. Papain digestion of antibodies produces two identical antigen-binding fragments called "Fab" fragments, each with a single antigen-binding site, and a residual "Fc" fragment, so called because of its ability to crystallize readily. The Fab fragment also contains the constant domain of the light chain and the $C_H1$ domain of the heavy chain. Pepsin treatment yields a $F(ab')_2$ fragment that has two antigen-binding sites and is still capable of cross-linking antigen.

Fab' fragments differ from Fab fragments by the presence of a few additional residues at the C-terminus of the $C_H1$ domain, including one or more cysteines from the antibody hinge region. Fab-SH is the designation herein for a Fab' in which the cysteine residue(s) of the constant domains bear a free thiol group. $F(ab')_2$ antibody fragments are pairs of Fab' fragments linked by cysteine residues in the hinge region. Other chemical couplings of antibody fragments are also known.

"Fv" is a minimum antibody fragment that contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody, in which the domains are present in a single polypeptide chain and which is capable of recognizing and binding antigen. The scFv polypeptide optionally contains a polypeptide linker positioned between the $V_H$ and $V_L$ domains that enables the scFv to form a desired three-dimensional structure for antigen binding (see, e.g., Pluckthun, 1994, In *The Pharmacology of monoclonal Antibodies*, Vol. 113, Rosenburg and Moore eds., Springer-Verlag, New York, pp. 269-315).

The term "diabodies" refers to small antibody fragments having two antigen-binding sites. Each fragment contains a heavy chain variable domain ($V_H$) concatenated to a light chain variable domain ($V_L$). By using a linker that is too short to allow pairing between the two domains on the same chain, the linked $V_H$-$V_L$ domains are forced to pair with complementary domains of another chain, creating two antigen-binding sites. Diabodies are described more fully, for example, in EP 404,097; WO 93/11161; and Hollinger et al., 1993, *Proc. Natl. Acad. Sci. USA* 90: 6444-6448.

The term "linear antibodies" refers to antibodies that comprise a pair of tandem Fd segments ($V_H$-$C_H1$-$V_H$-$C_H1$) that form a pair of antigen binding regions. Linear antibodies can be bispecific or monospecific as described in, for example, Zapata et al. 1995, *Protein Eng.* 8(10):1057-1062.

A humanized antibody or a humanized antibody fragment includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence is referred to herein as an "import" sequence, which is typically taken from an "import" antibody domain, particularly a variable domain. In general, a humanized antibody includes at least the CDRs or HVLs of a non-human antibody, inserted between the FRs of a human heavy or light chain variable domain. In certain aspects, a humanized anti-CD40 antibody contains CDR and/or HVL residues or sequences derived from the murine monoclonal antibody S2C6 inserted between the FRs of human consensus sequence heavy and light chain variable domains.

In another aspect, a humanized anti-CD40 antibody comprises substantially all of at least one, and typically two, variable domains (such as contained, for example, in Fab, Fab', F(ab')$_2$, Fabc, and Fv fragments) in which all, or substantially all, of the CDRs correspond to those of a non-human immunoglobulin and all, or substantially all, of the FRs are those of a human immunoglobulin consensus sequence. In another aspect, a humanized anti-CD40 antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_H1$, hinge, $C_H2$, $C_H3$, and/or $C_H4$ regions of the heavy chain, as appropriate.

A humanized anti-CD40 antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibit cytotoxic activity, and the isotype is typically $IgG_1$. Where such cytotoxic activity is not desirable, the constant domain may be of another isotype, e.g., $IgG_2$. An alternative humanized anti-CD40 antibody can comprise sequences from more than one immunoglobulin class or isotype, and selecting particular constant domains to optimize desired effector functions is within the ordinary skill in the art.

The FRs and CDRs, or HVLs, of a humanized anti-CD40 antibody need not correspond precisely to the parental sequences. For example, one or more residues in the import CDR, or HVL, or the consensus FR sequence may be altered (e.g., mutagenized) by substitution, insertion or deletion such that the resulting amino acid residue is no longer identical to the original residue in the corresponding position in either parental sequence. Such alterations, however, typically will not be extensive. Usually, at least 75% of the humanized antibody residues will correspond to those of the parental consensus FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). Additional residues include $V_L$ residues 43 and 85, and $V_H$ residues 43 and 60, as disclosed in U.S. Pat. No. 6,407,213, which is hereby incorporated by reference in its entirety. While these residues are indicated for human IgG only, they are applicable across species. Import antibody residues that are reasonably expected to be involved in interchain interactions are selected for substitution into the consensus sequence.

The terms "consensus sequence" and "consensus antibody" as used herein refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Provided are consensus human structures and consensus structures which consider other species in addition to human. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Useful consensus sequences include a human variable light chain kappa I consensus sequence (SEQ ID NO:13) and a human variable heavy chain subgroup III consensus sequence (SEQ ID NO:2), derived from the data provided in Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-CD40 antibodies. See, for example, U.S. Pat. Nos. 6,037,454 and 6,054,297. In certain embodiments, the FR used to prepare the humanized antibodies were derived from consensus sequences for a human variable light chain kappa I consensus sequence and for a human variable heavy chain subgroup III consensus sequence.

As used herein, "variant", "anti-CD40 variant", "humanized anti-CD40 variant", or "variant humanized anti-CD40" each refers to a humanized anti-CD40 antibody having at least a heavy chain variable CDR or HVL sequence derived from the murine monoclonal antibody S2C6 and FR sequences derived from human consensus sequences. Variants include those having one or more amino acid changes in one or both light chain or heavy chain variable domains, provided that the amino acid change does not substantially impair binding of the antibody to CD40. Humanized anti-CD40 variants typically include amino acid substitutions that improve antibody performance by allowing improved folding of the antibody molecule.

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified:

(a) to greater than 95% isolation by weight of antibody as determined by the Lowry method, and in another aspect, more than 99% isolation by weight, or (b) to a degree of isolation sufficient to obtain at least 15 residues of N-terminal or internal amino acid sequence by use of a spinning cup sequenator, or (c) to homogeneity by SDS-PAGE under reducing or non-reducing conditions as visualized using Coomassie blue or, preferably, silver stain.

An isolated antibody includes an antibody in situ within recombinant cells, since at least one component of the antibody's natural environment will not be present. Ordinarily however, an isolated antibody will be prepared by at least one purification step.

The term "antibody performance" refers to factors that contribute to antibody recognition of antigen or the effectiveness of an antibody in vivo. Changes in the amino acid sequence of an antibody can affect antibody properties such as folding, and can influence physical factors such as initial rate of antibody binding to antigen ($v_o$), dissociation constant of the antibody from antigen (Kd), affinity constant of the antibody for the antigen, conformation of the antibody, protein stability, and half life of the antibody.

The term "epitope tagged" when used herein, refers to an anti-CD40 antibody fused to an "epitope tag". An "epitope tag" is a polypeptide having a sufficient number of amino acids to provide an epitope for antibody production, yet is designed such that it does not interfere with the desired activity of the humanized anti-CD40 antibody. The epitope tag is usually sufficiently unique such that an antibody raised against the epitope tag does not substantially cross-react with other epitopes. Suitable tag polypeptides generally contain at least 6 amino acid residues and usually contain about 8 to 50 amino acid residues, or about 9 to 30 residues. Examples of epitope tags and the antibody that binds the epitope include the flu HA tag polypeptide and its antibody 12CA5 (Field et al., 1988 *Mol. Cell. Biol.* 8: 2159-2165; c-myc tag and 8F9, 3C7, 6E10, G4, B7 and 9E10 antibodies thereto (Evan et al., 1985, *Mol. Cell. Biol.* 5(12):3610-3616; and Herpes simplex virus glycoprotein D (gD) tag and its antibody (Paborsky et al. 1990, *Protein Engineering* 3(6): 547-553). In certain embodiments, the epitope tag is a "salvage receptor binding epitope". As used herein, the term "salvage receptor binding epitope" refers to an epitope of the Fc region of an IgG molecule (such as $IgG_1$, $IgG_2$, $IgG_3$, or $IgG_4$) that is responsible for increasing the in vivo serum half-life of the IgG molecule.

The term "cytotoxic agent" refers to a substance that inhibits or prevents the function of cells and/or causes destruction of cells. The term is intended to include radioactive isotopes (such as $I^{131}$, $I^{125}$, $Y^{90}$, and $Re^{186}$), chemotherapeutic agents, and toxins such as enzymatically active toxins of bacterial, fungal, plant, or animal origin, and fragments thereof. Such cytotoxic agents can be coupled to an antibody, e.g., a humanized anti-CD40 antibody, using known, standard procedures, and used, for example, to treat a patient indicated for therapy with the antibody.

A "chemotherapeutic agent" is a chemical compound useful in the treatment of cancer. Examples of chemotherapeutic agents include alkylating agents such a thiotepa and cyclosphosphamide (CYTOXAN™); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatin, auristatins, (including analogues monomethyl-auristatin E and monomethyl-auristatin F); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phiI1, see for example, *Agnew, Chem. Intl. Ed. Engl.*, 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine;

mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above.

The term "prodrug" as used herein refers to a precursor or derivative form of a pharmaceutically active substance that is less cytotoxic to tumor cells compared to the parent drug and is capable of being enzymatically activated or converted into the more active form. See, for example, Wilman, 1986, "Prodrugs in Cancer Chemotherapy", In *Biochemical Society Transactions*, 14, pp. 375-382, 615th Meeting Belfast and Stella et al., 1985, "Prodrugs: A Chemical Approach to Targeted Drug Delivery, In: "*Directed Drug Delivery*, Borchardt et al., (ed.), pp. 247-267, Humana Press. Useful prodrugs include, but are not limited to, phosphate-containing prodrugs, thiophosphate-containing prodrugs, sulfate-containing prodrugs peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

The term "label" refers to a detectable compound or composition that is conjugated directly or indirectly to the antibody. The label may itself be detectable (e.g., radioisotope labels or fluorescent labels) or, in the case of an enzymatic label, may catalyze chemical alteration of a substrate compound or composition that is detectable. Labeled humanized anti-CD40 antibody can be prepared and used in various applications including in vitro and in vivo diagnostics.

A "liposome" is a small vesicle composed of various types of lipids, phospholipids, and/or surfactant. Liposomes are useful for delivery to a mammal of a compound or formulation, such as a humanized anti-CD40 antibody disclosed herein, optionally, coupled to or in combination with one or more pharmaceutically active agents. The components of the liposome are commonly arranged in a bilayer formation, similar to the lipid arrangement of biological membranes.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "control sequences" refers to polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of humanized anti-CD40 antibody in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers. It is also understood that all progeny may not be precisely identical in DNA content, due to deliberate or naturally occurring mutations. Mutant progeny that have the same function or biological activity as screened for in the originally transformed cell are included. Where distinct designations are intended, it will be clear from the context.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-CD40 antibody described herein. This includes chronic and acute disorders or diseases including those pathological conditions that predispose the mammal to the disorder in question. Non-limiting examples or disorders to be treated herein include cancer, hematological malignancies, benign and malignant tumors, leukemias and lymphoid malignancies and inflammatory, angiogenic and immunologic disorders.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia.

As used herein, the term "CD40-associated disorder" or "CD40-associated disease" refers to a condition in which modification or elimination of cells expressing CD40 is indicated. These include CD40-expressing cells demonstrating abnormal proliferation or CD40-expressing cells that are associated with cancerous or malignant growth. More particular examples of cancers that demonstrate abnormal expression of CD40 antigen include B lymphoblastoid cells, Burkitt's lymphoma, multiple myeloma, T cell lymphomas, Kaposi's sarcoma, osteosarcoma, epidermal and endothelial tumors, pancreatic, lung, breast, ovarian, colon, prostate, head and neck, skin (melanoma), bladder, and kidney cancers. Such disorders include, but are not limited to, leukemias, lymphomas, including B cell lymphoma and non-Hodgkin's lymphoma, multiple myeloma, Waldenstrom's macroglobulinemia; solid tumors, including sarcomas, such as osteosarcoma, Ewing's sarcoma, malignant melanoma, adenocarcinoma, including ovarian adenocarcinoma, Kaposi's sarcoma/Kaposi's tumor and squamous cell carcinoma.

A CD40-associated disorder also includes diseases and disorders of the immune system, such as auto-immune disorders and inflammatory disorders. Such conditions include, but are not limited to, rheumatoid arthritis (RA), systemic lupus erythematosus (SLE), scleroderma, Sjogren's syndrome, multiple sclerosis, inflammatory bowel disease (e.g., ulcerative colitis and Crohn's disease), pulmonary inflammation, asthma, and idiopathic thrombocytopenic purara (ITP).

The phrase "arrests the growth of" or "growth inhibitory" when used herein refers to inhibiting growth or proliferation of a cell, especially a neoplastic cell type expressing the CD40 antigen. Thus, growth inhibition, for example, significantly reduces the percentage of neoplastic cells in S phase.

The term "intravenous infusion" refers to introduction of an agent into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an active agent having beneficial patient outcome, for example, a growth arrest effect or causes the deletion of the cell. In one aspect, the therapeutically effective amount has apoptotic activity, or is capable of inducing cell death. In another aspect, the therapeutically effective amount refers to a target serum concentration that has been shown to be effective in, for example, slowing disease progression. Efficacy can be measured in conventional ways, depending on the condition to be treated. For example, in neoplastic diseases or disorders characterized by cells expressing CD40, efficacy can be measured by assessing the time to disease progression (TTP), or determining the response rates (RR).

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein.

The term "package insert" is used to refer to instructions customarily included in commercial packages of therapeutic products, that contain information about the indications, usage, administration, contraindications and/or warnings concerning the use of such therapeutic products.

The abbreviation "AFP" refers to dimethylvaline-valine-dolaisoleuine-dolaproine-phenylalanine-p-phenylenediamine.

The abbreviation "MMAE" refers to monomethyl auristatin E.

The abbreviation "AEB" refers to an ester produced by reacting auristatin E with paraacetyl benzoic acid.

The abbreviation "AEVB" refers to an ester produced by reacting auristatin E with benzoylvaleric acid.

The abbreviation "MMAF" refers to dovaline-valine-dolaisoleunine-dolaproine-phenylalanine.

Antibodies

Described and disclosed herein are humanized anti-CD40 antibodies, and compositions and articles of manufacture comprising a humanized anti-CD40 antibody. Also described are binding agents that include an antigen-binding fragment of a humanized anti-CD40 antibody. The humanized anti-CD40 antibodies and binding agents can arrest the growth of cells, cause the deletion of cells expressing CD40 or otherwise induce or cause a cytotoxic or cytostatic effect on target cells. The humanized anti-CD40 antibodies and binding agents can be used in the treatment of a variety of diseases or disorders characterized by the proliferation of cells expressing the CD40 surface antigen.

A humanized anti-CD40 antibody and a CD40 binding agent each includes at least a portion that specifically recognizes a CD40 epitope (i.e., an antigen-binding fragment). In some embodiments a humanized anti-CD40 antibody or a CD40 binding agent includes an antigen-binding fragment that competes for binding with antibody S2C6.

In some embodiments, the antigen-binding fragment can, for example, block proliferation or otherwise arrest the growth of a cell or cause its depletion, death, or otherwise its deletion, for example, through binding the CD40 surface antigen. For example, in T and B cell malignancies, antitumor effects (e.g., growth arrest with or without cell deletion or apoptosis) often result when malignant cells are exposed to stimuli that lead to activation of normal lymphocytes. This activation-induced growth arrest has been observed with signals through either antigen receptors or costimulatory receptors (see, e.g., Ashwell et al., 1987, *Science* 237:61; Bridges et al., 1987, *J. Immunol.* 139:4242; Page and Defranco, 1988, *J. Immunol.* 140:3717; and Beckwith et al., 1990, *J. Natl. Cancer Inst.* 82:501). CD40 stimulation, as a result of specific binding by either antibody or soluble ligand, inhibits B cell lymphoma growth (see, e.g., Funakoshi et al., 1994, *Blood* 83:2787-2794). Agents that inhibit malignant cell growth in this way and that are directed against the CD40 surface antigen are examples of appropriate agents.

CD40 specific agents include an antigen-binding fragment of a humanized anti-CD40 antibody that binds to CD40 (e.g., human CD40 or a variant thereof). The CD40 specific agents and antibodies can be optionally conjugated with or fused to a cytotoxic or chemotherapeutic agent. In aspects where the humanized antibody binds to the CD40 surface antigen and causes depletion of the CD40 expressing cell types, binding is generally characterized by homing to the CD40 surface antigen cell in vivo. Suitable binding agents bind the CD40 antigen with sufficient affinity and/or avidity such that the CD40 specific agent is useful as a therapeutic agent by specifically targeting a cell expressing the antigen.

In one aspect, the agent is a humanized antibody containing the CDRs of the murine monoclonal antibody S2C6. (The S2C6 antibody is described, for example, by Paulie et al., 1984, *Cancer Immunol. Immunother.* 17:165-179.) The S2C6 antibody has been shown to exert an agonist activity on human peripheral B cells as demonstrated by the antibody's ability to stimulate primary B cell proliferation in a dose dependent manner (see, e.g., Paulie et al., 1989, *J. Immunol.* 142:590-595), as well as anti-neoplastic activity in vivo (see, e.g., U.S. Pat. No. 6,838,261).

In some aspects, the humanized antibody increases the binding of CD40 ligand to CD40 by at least 45%, by at least 50%, by at least 60% or by at least 75%. A method of determining increases in binding of CD40 ligand to CD40 are disclosed in U.S. Pat. No. 6,838,261 (the disclosure of which is incorporated by reference herein).

In some embodiments, the humanized anti-CD40 antibodies, including antigen-binding fragments thereof, such as heavy and light chain variable domains, comprise an amino acid sequence of the residues derived from the CDRs or HVLs of the S2C6 murine antibody (see, e.g., U.S. Pat. No. 6,838,261) and amino acid residues derived from framework regions of a human immunoglobulin. In one aspect, the human framework region amino acids are derived from human consensus sequences for the heavy chain subgroup III variable domain and the kappa light chain variable as described in U.S. Pat. No. 6,037,454. The humanized anti-CD40 antibodies optionally include specific amino acid substitutions in the consensus framework regions.

The specific substitution of amino acid residues in these framework positions can improve various aspects of antibody performance including binding affinity and/or stability, over that demonstrated in humanized antibodies formed by "direct swap" of CDRs or HVLs into the human consensus framework regions, as shown in the examples below.

In some embodiments, the humanized anti-CD40 antibodies disclosed herein comprise at least a heavy or light chain variable domain comprising the CDRs or HVLs of the murine monoclonal antibody S2C6 and the FRs of the human consensus heavy and light chain variable domains having the specific substitutions described in Table 5. An alignment of the variable heavy chain amino acid sequences having substitutions and variable light chain amino acid sequences having substitutions are shown in Tables 3 and 4, respectively. These sequences include a heavy chain variable domain having the amino acid sequence of SEQ ID NO:3 and a light chain variable domain having the amino acid sequence of SEQ ID NO: 14.

In certain embodiments, the humanized anti-CD40 antibody is an antibody fragment. Various techniques have been developed for the production of antibody fragments. Fragments can be derived via proteolytic digestion of intact antibodies (see, e.g., Morimoto et al., 1992, *Journal of Biochemical and Biophysical Methods* 24:107-117; and Brennan et al., 1985, *Science* 229:81). Alternatively, the fragments can be produced directly in recombinant host cells. For example, Fab'-SH fragments can be directly recovered from *E. coli* and chemically coupled to form F(ab')$_2$ fragments (see, e.g., Carter et al., 1992, *Bio/Technology* 10:163-167). By another approach, F(ab')$_2$ fragments can be isolated directly from recombinant host cell culture. Other techniques for the production of antibody fragments will be apparent to the skilled practitioner.

Certain embodiments include an F(ab')$_2$ fragment of a humanized anti-CD40 antibody comprising a heavy chain variable domain amino acid sequence and a light chain variable domain amino acid sequence of SEQ ID NO:3 and SEQ ID NO:14, respectively; SEQ ID NO:4 and SEQ ID NO:14, respectively; SEQ ID NO:5 and SEQ ID NO: 14, respectively; SEQ ID NO:6 and SEQ ID NO: 14, respectively; SEQ ID NO:7 and SEQ ID NO: 14, respectively; SEQ ID NO:8 and SEQ ID NO: 14, respectively; SEQ ID NO:9 and SEQ ID NO:14, respectively; SEQ ID NO:6 and SEQ ID NO:15, respectively; SEQ ID NO:6 and SEQ ID NO: 16, respectively; SEQ ID NO:7 and SEQ ID NO: 16, respectively; SEQ ID NO:10 and SEQ. ID NO:14, respectively; SEQ ID NO:11 and SEQ ID NO:14, respectively; SEQ ID NO:10 and SEQ ID NO:16, respectively; or SEQ ID NO:11 and SEQ ID NO: 16, respectively. Such embodiments can include an intact antibody comprising such an F(ab')$_2$.

Other embodiments include a F(ab')$_2$ fragment of a humanized anti-CD40 antibody comprising a heavy chain variable domain amino acid sequence and a light chain variable domain amino acid sequence of SEQ ID NO:7 and SEQ ID NO:14, respectively; SEQ ID NO:6 and SEQ ID NO:16, respectively; SEQ ID NO:7 and SEQ ID NO: 16, respectively; SEQ ID NO: 10 and SEQ ID NO: 14, respectively; SEQ ID NO: 11 and SEQ ID NO:14, respectively; SEQ ID NO:10 and SEQ ID NO:16, respectively; and SEQ ID NO: 11 and SEQ ID NO:16, respectively.

Yet other embodiments include a F(ab')$_2$ fragment of a humanized anti-CD40 antibody comprising a heavy chain variable domain amino acid sequence and a light chain variable domain amino acid sequence of SEQ ID NO:7 and SEQ ID NO: 14, respectively; SEQ ID NO:6 and SEQ ID NO:16, respectively; SEQ ID NO:10 and SEQ ID NO: 16, respectively; and SEQ ID NO: 11 and SEQ ID NO: 16, respectively.

Some embodiments include a F(ab')$_2$ fragment of a humanized anti-CD40 antibody that contains a heavy chain variable domain comprising the amino acid sequence of SEQ ID NO:

10 and a light chain variable domain comprising the amino acid sequence of SEQ ID NO: 16.

In some embodiments, the antibody or antibody fragment includes a constant region that mediates effector function. The constant region can provide antibody-dependent cellular cytotoxicity (ADCC), antibody-dependent cellular phagocytosis (ADCP) and/or complement-dependent cytotoxicity (CDC) responses against a CD40-expressing target cell. The effector domain(s) can be, for example, an Fc region of an Ig molecule. Typically, the CD40 binding agent recruits and/or activates cytotoxic white blood cells (e.g., natural killer (NK) cells, phagocytotic cells (e.g., macrophages), and/or serum complement components).

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of IgM≈IgG$_1$≈IgG$_3$>IgG$_2$>IgG$_4$ and IgG$_1$≈IgG$_3$>IgG$_2$/IgM/IgG$_4$, respectively. Murine immunoglobulins mediate CDC and ADCC/ADCP generally in the order of murine IgM≈IgG$_3$>>IgG$_{2b}$>IgG$_{2a}$>>IgG$_1$ and IgG$_{2b}$>IgG$_{2a}$>IgG$_1$>>IgG$_3$, respectively. In another example, murine IgG$_{2a}$ mediates ADCC while both murine IgG$_{2a}$ and IgM mediate CDC.

Antibody Modifications

The humanized anti-CD40 antibodies and agents can include modifications of the humanized anti-CD40 antibody or antigen-binding fragment thereof. For example, it may be desirable to modify the antibody with respect to effector function, so as to enhance the effectiveness of the antibody in treating cancer, for example. One such modification is the introduction of cysteine residue(s) into the Fc region, thereby allowing interchain disulfide bond formation in this region. The homodimeric antibody thus generated can have improved internalization capability and/or increased complement-mediated cell killing and/or antibody-dependent cellular cytotoxicity (ADCC). See, for example, Caron et al., 1992, *J. Exp Med.* 176:1191-1195; and Shopes, 1992, *J. Immunol.* 148:2918-2922. Homodimeric antibodies having enhanced anti-tumor activity can also be prepared using heterobifunctional cross-linkers as described in Wolff et al., 1993, *Cancer Research* 53: 2560-2565. Alternatively, an antibody can be engineered to contain dual Fc regions, enhancing complement lysis and ADCC capabilities of the antibody. See Stevenson et al., 1989, *Anti-Cancer Drug Design* 3: 219-230.

Antibodies with improved ability to support ADCC have been generated by modifying the glycosylation pattern of their Fc region. This is possible since antibody glycosylation at the asparagine residue, N297, in the $C_H2$ domain is involved in the interaction between IgG and Fcγ receptors prerequisite to ADCC. Host cell lines have been engineered to express antibodies with altered glycosylation, such as increased bisecting N-acetylglucosamine or reduced fucose. Fucose reduction provides greater enhancement to ADCC activity than does increasing the presence of bisecting N-acetylglucosamine. Moreover, enhancement of ADCC by low fucose antibodies is independent of the FcγRIIIa V/F polymorphism.

Modifying the amino acid sequence of the Fc region of antibodies is an alternative to glycosylation engineering to enhance ADCC. The binding site on human IgG$_1$ for Fcγ receptors has been determined by extensive mutational analysis. This led to the generation of humanized IgG$_1$ antibodies with Fc mutations that increase the binding affinity for FcγRIIIa and enhance ADCC in vitro. Additionally, Fc variants have been obtained with many different permutations of binding properties, e.g., improved binding to specific FcγR receptors with unchanged or diminished binding to other FcγR receptors.

In some embodiments, the Fc region can be modified as described in U.S. Patent Application Publication Nos. 2006-0003412 and 2006-0008883, the disclosures of which are incorporated by reference herein.

Another aspect includes immunoconjugates comprising the humanized antibody or fragments thereof conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used to form useful immunoconjugates include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, the tricothecenes, and the like. A variety of radionuclides are available for the production of radioconjugated humanized anti-CD40 antibodies. Examples include $^{212}$Bi, $^{131}$I, $^{131}$In, $^{90}$Y, and $^{186}$Re.

Conjugates of the humanized anti-CD40 antibody and cytotoxic or chemotherapeutic agent can be made by known methods, using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., 1987, *Science* 238:1098. Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., International Publication WO 94/11026. Conjugates also can be formed with a cleavable linker, such as that disclosed in published EP Patent Application 0 624 377; the disclosure of which is incorporated by reference herein.

In another embodiment, the antibody may be conjugated to a "receptor" (such as streptavidin) for utilization in tumor pretargeting. In this procedure, the antibody-receptor conjugate is administered to a patient, followed by removal of unbound conjugate from the circulation using a clearing agent and then administration of a "ligand" that selectively binds the receptor (e.g., avidin), the ligand being conjugated to a cytotoxic agent (e.g., a radionuclide).

The humanized anti-CD40 antibodies disclosed herein can also be formulated as immunoliposomes. Liposomes containing the antibody are prepared by methods known in the art, such as described in Epstein et al., 1985, *Proc. Natl. Acad. Sci. USA* 82:3688; Hwang et al., 1980, *Proc. Natl. Acad. Sci. USA* 77:4030; and U.S. Pat. Nos. 4,485,045 and 4,544,545. Liposomes having enhanced circulation time are disclosed, for example, in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody disclosed herein can be conjugated to the liposomes as described in Martin et al., 1982, *J. Biol. Chem.* 257:286-288 via a disulfide interchange reaction. A chemotherapeutic agent (such as doxorubicin) is optionally contained within the liposome. See, e.g., Gabizon et al., 1989, *J. National Cancer Inst.* 81(19):1484.

The antibodies described and disclosed herein can also be used in ADEPT (Antibody-Directed Enzyme Prodrug Therapy) procedures by conjugating the antibody to a prodrug-activating enzyme that converts a prodrug (e.g., a peptidyl chemotherapeutic agent), to an active anti-cancer drug. See, for example, WO 81/01145, WO 88/07378, and U.S. Pat. No. 4,975,278. The enzyme component of the immunoconjugate useful for ADEPT is an enzyme capable of acting on a prodrug in such a way so as to covert it into its more active, cytotoxic form. Specific enzymes that are useful in ADEPT include, but are not limited to, alkaline phosphatase for converting phosphate-containing prodrugs into free drugs; arylsulfatase for converting sulfate-containing prodrugs into free drugs; cytosine deaminase for converting non-toxic 5-fluorocytosine into the anti-cancer drug, 5-fluorouracil; proteases, such as *serratia* protease, thermolysin, subtilisin, carboxypeptidases, and cathepsins (such as cathepsins B and L), for converting peptide-containing prodrugs into free drugs; D-alanylcarboxypeptidases, for converting prodrugs containing D-amino acid substituents; carbohydrate-cleaving enzymes such as β-galactosidase and neuraminidase for converting glycosylated prodrugs into free drugs; β-lactamase for converting drugs derivatized with β-lactams into free drugs; and penicillin amidases, such as penicillin V amidase or penicillin G amidase, for converting drugs derivatized at their amine nitrogens with phenoxyacetyl or phenylacetyl groups, respectively, into free drugs. Alternatively, antibodies having enzymatic activity ("abzymes") can be used to convert the prodrugs into free active drugs (see, for example, Massey, 1987, *Nature* 328: 457-458). Antibody-abzyme conjugates can be prepared by known methods for delivery of the abzyme to a tumor cell population, for example, by covalently binding the enzyme to the humanized anti-CD40 antibody/heterobifunctional crosslinking reagents discussed above. Alternatively, fusion proteins comprising at least the antigen binding region of an antibody disclosed herein linked to at least a functionally active portion of an enzyme as described above can be constructed using recombinant DNA techniques (see, e.g., Neuberger et al., 1984, *Nature* 312:604-608).

In certain embodiments, it may be desirable to use a humanized anti-CD40 antibody fragment, rather than an intact antibody, to increase tumor penetration, for example. It may be desirable to modify the antibody fragment in order to increase its serum half life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, covalent modifications of the humanized anti-CD40 antibody are also included. They may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody.

Removal of any carbohydrate moieties present on the antibody can be accomplished chemically or enzymatically. Chemical deglycosylation is described by Hakimuddin et al., 1987, *Arch. Biochem. Biophys.* 259:52 and by Edge et al., 1981, *Anal. Biochem.*, 118:131. Enzymatic cleavage of carbohydrate moieties on antibodies can be achieved by the use of a variety of endo- and exo-glycosidases as described by Thotakura et al., 1987, *Meth. Enzymol* 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. No. 4,640,835, U.S. Pat. No. 4,496,689, U.S. Pat. No. 4,301,144, U.S. Pat. No. 4,670,417, U.S. Pat. No. 4,791,192 and U.S. Pat. No. 4,179,337.

Humanization and Amino Acid Sequence Variants

Example 1 below describes procedures for humanization of an anti-CD40 antibody while Example 2 describes variants. In certain embodiments, it may be desirable to generate amino acid sequence variants of these humanized antibodies, particularly where these improve the binding affinity or other biological properties of the humanized antibody.

Amino acid sequence variants of the anti-CD40 antibody can be prepared by introducing appropriate nucleotide changes into the anti-CD40 antibody DNA, or by peptide synthesis. Such variants include, for example, deletions from, and/or insertions into and/or substitutions of, residues within the amino acid sequences of the anti-CD40 antibodies of the examples herein. Any combination of deletions, insertions, and substitutions is made to arrive at the final construct, provided that the final construct possesses the desired characteristics. The amino acid changes also may alter post-translational processes of the humanized or variant anti-CD40 antibody, such as changing the number or position of glycosylation sites.

A useful method for identification of certain residues or regions of the anti-CD40 antibody that are preferred locations for mutagenesis is called "alanine scanning mutagenesis," as described by Cunningham and Wells (*Science*, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with CD40 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-CD40 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-CD40 antibody fused to an epitope tag. Other insertional variants of the anti-CD40 antibody molecule include a fusion to the N- or C-terminus of the anti-CD40 antibody of an enzyme or a polypeptide which increases the serum half-life of the antibody.

Another type of variant is an amino acid substitution variant. These variants have at least one amino acid residue in the anti-CD40 antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions", or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
  (1) hydrophobic: norleucine, met, ala, val, leu, ile;
  (2) neutral hydrophilic: cys, ser, thr;
  (3) acidic: asp, glu;
  (4) basic: asn, gln, his, lys, arg;
  (5) residues that influence chain orientation: gly, pro; and
  (6) aromatic: trp, tyr, phe.

Non-conservative substitutions will entail exchanging a member of one of these classes for another class.

Any cysteine residue not involved in maintaining the proper conformation of the humanized or variant anti-CD40 antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human CD40. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-CD40 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-CD40 antibody.

Human Antibodies

As an alternative to humanization, human antibodies can be generated. For example, transgenic animals (e.g., mice) can be used that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. As an alternative to humanization, human antibodies can be generated. For example, transgenic animals (e.g., mice) can be used that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 1993, *Proc. Natl. Acad. Sci. USA* 90:2551; Jakobovits et al., 1993, *Nature* 362:255-258; Bruggermann et al., 1993, *Year in Immuno.* 7:33; and U.S. Pat. Nos. 5,591,669; 5,589,369; 5,545,807; 6,075,181; 6,150,584; 6,657,103; and 6,713,610.

Alternatively, phage display technology (see, e.g., McCafferty et al., 1990, *Nature* 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson and Chiswell, 1993, *Current Opinion in Structural Biology* 3:564-571. Several sources of V-gene segments can be used for phage display. Clackson et al., 1991, *Nature* 352:624-628 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., 1991, *J. Mol. Biol.* 222:581-597, or Griffith et al., 1993, *EMBO J.* 12:725-734. See also U.S. Pat. Nos. 5,565,332 and 5,573,905. As discussed above, human antibodies may also be generated by in vitro activated B cells (see U.S. Pat. Nos. 5,567,610 and 5,229,275).

Polynucleotides, Vectors, Host Cells, and Recombinant Methods

Other embodiments encompass isolated polynucleotides that comprise a sequence encoding a humanized anti-CD40 antibody, vectors, and host cells comprising the polynucleotides, and recombinant techniques for production of the humanized antibody. The isolated polynucleotides can encode any desired form of the anti-CD40 antibody including, for example, full length monoclonal antibodies, Fab, Fab', F(ab')$_2$, and Fv fragments, diabodies, linear antibodies, single-chain antibody molecules, and multispecific antibodies formed from antibody fragments.

Some embodiments include isolated polynucleotides comprising sequences that encode an antibody or antibody fragment having the heavy chain variable region amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO: 11. Some embodiments include isolated polynucleotides comprising sequences that encode an antibody or antibody fragment having the light chain variable domain amino acid sequence of SEQ ID NO:14, SEQ ID NO:15, or SEQ ID NO:16.

In one aspect, the isolated polynucleotide sequence(s) encodes an antibody or antibody fragment having a heavy chain variable domain and a light chain variable region comprising the amino acid sequences of SEQ ID NO:3 and SEQ ID NO:14, respectively; SEQ ID NO:4 and SEQ ID NO:14, respectively; SEQ ID NO:5 and SEQ ID NO:14, respectively; SEQ ID NO:6 and SEQ ID NO:14, respectively; SEQ ID NO:7 and SEQ ID NO:14, respectively; SEQ ID NO:8 and SEQ ID NO:14, respectively; SEQ ID NO:9 and SEQ ID NO:14, respectively; SEQ ID NO:6 and SEQ ID NO:15, respectively; SEQ ID NO:6 and SEQ ID NO:16, respectively; SEQ ID NO:7 and SEQ ID NO:16, respectively; SEQ ID NO:10 and SEQ ID NO:14, respectively; SEQ ID NO:11 and SEQ ID NO:14, respectively; SEQ ID NO:10 and SEQ ID NO: 16, respectively; or SEQ ID NO:11 and SEQ ID NO:16, respectively.

In another aspect, the isolated polynucleotide sequence(s) encodes an antibody or antibody fragment having a heavy chain variable domain and a light chain variable domain comprising the amino acid sequences of SEQ ID NO:7 and SEQ ID NO: 14, respectively; SEQ ID NO:6 and SEQ ID NO: 16, respectively; SEQ ID NO:7 and SEQ ID NO: 16, respectively; SEQ ID NO: 10 and SEQ ID NO: 14, respectively; SEQ ID NO: 11 and SEQ ID NO:14, respectively; SEQ ID NO:10 and SEQ ID NO:16, respectively; and SEQ ID NO: 11 and SEQ ID NO:16, respectively.

In yet another aspect, the isolated polynucleotide sequence(s) encodes an antibody or antibody fragment having a heavy chain variable domain and a light chain variable domain comprising the amino acid sequences of SEQ ID NO:7 and SEQ ID NO: 14, respectively; SEQ ID NO:6 and SEQ ID NO: 16, respectively; SEQ ID NO: 10 and SEQ ID NO: 16, respectively; and SEQ ID NO: 11 and SEQ ID NO: 16, respectively.

In yet another aspect, the isolated polynucleotide sequence(s) encodes an antibody or antibody fragment having a heavy chain variable domain and a light chain variable domain comprising the amino acid sequences of SEQ ID NO:10 and a light chain variable domain comprising the amino acid sequence of SEQ ID NO: 16.

The polynucleotide(s) that comprise a sequence encoding a humanized anti-CD40 antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The humanized anti-CD40 antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the humanized anti-CD40 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-CD40 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-μ plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin.

Another example of suitable selectable markers for mammalian cells are those that enable the identification of cells competent to take up a nucleic acid encoding a humanized anti-CD40 antibody, such as DHFR (dihydrofolate reductase), thymidine kinase, metallothionein-I and -II (such as primate metallothionein genes), adenosine deaminase, ornithine decarboxylase, and the like.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-CD40 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

A suitable selection gene for use in yeast is the TRP1 gene present in the yeast plasmid YRp7 (Stinchcomb et al., 1979, *Nature* 282: 39). The TRP1 gene provides a selection marker for a mutant strain of yeast lacking the ability to grow in tryptophan, for example, ATCC No. 44076 or PEP4-1 (Jones, 1977, *Genetics* 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, *Bio/Technology* 8:135). Stable multi-copy expression vectors for secretion of mature recombinant human serum albumin by industrial strains of *Kluyveromyces* have also been disclosed (Fleer et al., 1991, *Bio/Technology* 9:968-975).

Expression and cloning vectors usually contain a promoter that is recognized by the host organism and is operably linked to the nucleic acid molecule encoding an anti-CD40 antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-CD40 antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Humanized anti-CD40 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human β-interferon cDNA in mouse cells under the control of a thymidine kinase promoter from herpes simplex virus. Alternatively, the rous sarcoma virus long terminal repeat can be used as the promoter.

Transcription of a DNA encoding a humanized anti-CD40 antibody disclosed herein by higher eukaryotes is often increased by inserting an enhancer sequence into the vector. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the humanized anti-CD40 antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-CD40 antibody. One useful transcription termination component is the bovine growth hormone polyadenylation region. See WO94/11026 and the expression vector disclosed therein. In some embodiments, humanized anti-CD40 antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for humanized anti-CD40 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated humanized anti-CD40 antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

In another aspect, expression of humanized anti-CD40 is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, *J. Gen Virol.* 36: 59), baby hamster kidney cells (BHK, ATCC CCL 10), Chinese hamster ovary cells/–DHFR1 (CHO, Urlaub et al., 1980, *Proc. Natl. Acad. Sci. USA* 77: 4216; e.g., DG44), mouse sertoli cells (TM4, Mather, 1980, *Biol. Reprod.* 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, *Annals N.Y. Acad. Sci.* 383: 44-68), MRC 5 cells, FS4 cells, and human hepatoma line (Hep G2).

Host cells are transformed with the above-described expression or cloning vectors for humanized anti-CD40 antibody production and cultured in conventional nutrient media modified as appropriate for inducing promoters, selecting transformants, or amplifying the genes encoding the desired sequences.

The host cells used to produce a humanized anti-CD40 antibody described herein may be cultured in a variety of media. Commercially available media such as Ham's F10

(Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, *Meth. Enz.* 58: 44, Barnes et al., 1980, *Anal. Biochem.* 102: 255, U.S. Pat. No. 4,767,704, U.S. Pat. No. 4,657,866, U.S. Pat. No. 4,927,762, U.S. Pat. No. 4,560,655, U.S. Pat. No. 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, *Bio/Technology* 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 *J. Immunol. Meth.* 62:1-13). Protein G is recommended for all mouse isotypes and for human gamma3 (see, e.g., Guss et al., 1986 *EMBO J.* 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Hybridization Conditions

Also included are nucleic acids that hybridize under low, moderate, and high stringency conditions, as defined herein, to all or a portion (e.g., the portion encoding the variable region) of the nucleotide sequence represented by SEQ ID NO: 17, or its complement, or SEQ ID NO:20 or its complement. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-CD40 polypeptide (e.g., a heavy chain or light chain variable region), or its complement. Hybridizing nucleic acids of the type described herein can be used, for example, as a cloning probe, a primer, e.g., a PCR primer, or a diagnostic probe.

By way of example and not limitation, procedures using conditions of low stringency are as follows (see also Shilo and Weinberg, 1981, *Proc. Natl. Acad. Sci. USA* 78:6789-6792). In one embodiment, filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. In another embodiment, an example of low stringency conditions includes hybridization in a buffer comprising 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt/vol) dextran sulfate, for 18-20 hours at 40° C., washing in a buffer consisting of 2×SSC, 25 mM Tris-HCl (pH 7.4), 5 mM EDTA, and 0.1% SDS, for 1.5 hours at 55° C., and washing in a buffer consisting of 2×SSC, 25 mM Tris-HCl (pH 7.4), 5 mM EDTA, and 0.1% SDS, for 1.5 hours at 60° C. Other conditions of low stringency that may be used are well known in the art (e.g., as employed for cross-species hybridizations).

By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency that may be used are well known in the art.

By way of example and not limitation, procedures using conditions of moderate stringency are as follows: Filters containing DNA are pretreated for 6 hours at 55° C. in a solution containing 6×SSC, 5×Denhardt's solution, 0.5% SDS and 100 µg/ml denatured salmon sperm DNA. Hybridizations are carried out in the same solution with 5-20×10$^6$ cpm $^{32}$P-labeled probe. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Washing of filters is done at 37° C. for 1 hour in a solution containing 2×SSC, 0.1% SDS. Other conditions of moderate stringency that may be used are well-known in the art (see, e.g., Sambrook et al., 1989, *Molecular Cloning, A Laboratory Manual*, 2d Ed., Cold Spring Harbor Laboratory Press, Cold Spring Harbor, N.Y.; Sambrook et al., 2001; Molecular Cloning, A Laboratory Manual, 3rd ed., Cold Spring Harbor Publish., Cold Spring Harbor, N.Y.; see also Ausubel et al., eds., in *Current Protocols in Molecular Biology* series of laboratory technique manuals, 1987-1999, Current Protocols, © 1994-199 John Wiley and Sons, Inc.).

Some embodiments include isolated polynucleotides including sequences that encode an antibody or antibody fragment having the heavy chain variable region amino acid sequence that is at least 80%, at least 90%, at least 95%, at least 98%, or at least 99% identical to the amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO: 11. Some embodiments include isolated polynucleotides including sequences that encode an antibody or antibody fragment having the light chain variable domain amino acid sequence that is at least 80%, at least 90%, at least 95%, at least 98%, or at least 99% identical to the amino acid sequence of SEQ ID NO:14, SEQ ID NO:15, or SEQ ID NO:16.

In one aspect, the isolated polynucleotide sequence(s) encodes an antibody or antibody fragment having a heavy chain variable domain and a light chain variable region, each including an amino acid sequence that is at least 80%, at least 90%, at least 95%, at least 98%, or at least 99% identical to the amino acid sequence of SEQ ID NO:3 and SEQ ID NO:14, respectively; SEQ ID NO:4 and SEQ ID NO:14, respectively; SEQ ID NO:5 and SEQ ID NO:14, respectively; SEQ ID NO:6 and SEQ ID NO:14, respectively; SEQ ID NO:7 and SEQ ID NO:14, respectively; SEQ ID NO:8 and SEQ ID NO:14, respectively; SEQ ID NO:9 and SEQ ID NO:14, respectively; SEQ ID NO:6 and SEQ ID NO:15, respectively; SEQ ID NO:6 and SEQ ID NO:16, respectively; SEQ ID NO:7 and SEQ ID NO:16, respectively; SEQ ID NO:10 and SEQ ID NO:14, respectively; SEQ ID NO:11 and SEQ ID NO:14, respectively; SEQ ID NO:10 and SEQ ID NO:16, respectively; or SEQ ID NO:11 and SEQ ID NO:16, respectively.

In another aspect, the isolated polynucleotide sequence(s) encodes an antibody or antibody fragment having a heavy chain variable domain and a light chain variable domain, each including an amino acid sequence that is at least 80%, at least 90%, at least 95%, at least 98%, or at least 99% identical to the amino acid sequence of SEQ ID NO:7 and SEQ ID NO:14, respectively; SEQ ID NO:6 and SEQ ID NO:16, respectively; SEQ ID NO:7 and SEQ ID NO:16, respectively; SEQ ID NO:10 and SEQ ID NO:14, respectively; SEQ ID NO:11 and SEQ ID NO:14, respectively; SEQ ID NO:10 and SEQ ID NO:16, respectively; and SEQ ID NO: 1 and SEQ ID NO:16, respectively.

In yet another aspect, the isolated polynucleotide sequence(s) encodes an antibody or antibody fragment having a heavy chain variable region and a light chain variable region, each including an amino acid sequence that is at least 80%, at least 90%, at least 95%, at least 98%, or at least 99% identical to the amino acid sequence of SEQ ID NO:7 and SEQ ID NO:14, respectively; SEQ ID NO:6 and SEQ ID NO:16, respectively; SEQ ID NO:10 and SEQ ID NO:16, respectively; and SEQ ID NO: 11 and SEQ ID NO:16, respectively.

In yet another aspect, the isolated polynucleotide sequence(s) encodes an antibody or antibody fragment having a heavy chain variable region and a light chain variable region, each including an amino acid sequence that is at least 80%, at least 90%, at least 95%, at least 98%, or at least 99% identical to the amino acid sequence of SEQ ID NO:10 and SEQ ID NO:16, respectively.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402.

Non-Therapeutic Uses

The antibodies described herein are useful as affinity purification agents. In this process, the antibodies are immobilized on a solid phase such a Sephadex resin or filter paper, using methods well known in the art. The immobilized antibody is contacted with a sample containing the CD40 protein (or fragment thereof) to be purified, and thereafter the support is washed with a suitable solvent that will remove substantially all the material in the sample except the CD40 protein, which is bound to the immobilized antibody. Finally, the support is washed with another suitable solvent, such as glycine buffer, pH 5.0 that will release the CD40 protein from the antibody.

Humanized anti-CD40 antibodies are also useful in diagnostic assays to detect and/or quantify CD40 protein, for example, detecting CD40 expression in specific cells, tissues, or serum.

For diagnostic applications, the antibody typically will be labeled with a detectable moiety. Numerous labels are available which can be generally grouped into the following categories:

(a) Radioisotopes, for example, such as $^{35}S$, $^{14}C$, $^{125}I$, $^{3}H$, and $^{131}I$. The antibody can be labeled with the radioisotope, using the techniques described in, for example, *Current Protocols in Immunology*, Volumes 1 and 2, 1991, Coligen et al., Ed. Wiley-Interscience, New York, N.Y., Pubs. Radioactivity can be measured, for example, by scintillation counting.

(b) Fluorescent labels such as rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in *Current Protocols in Immunology*, supra, for example. Fluorescence can be quantified using a fluorimeter.

(c) Various enzyme-substrate labels are available (see, e.g., U.S. Pat. No. 4,275,149 provides a review of some of these). The enzyme generally catalyzes a chemical alteration of the chromogenic substrate that can be measured using various techniques. For example, the enzyme may catalyze a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor. Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in *Methods in Enzym.* (J. Langone & H. Van Vunakis, eds.), Academic press, N.Y., 73: 147-166.

Examples of enzyme-substrate combinations include, for example:

(a) Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB);

(b) alkaline phosphatase (AP) with para-Nitrophenyl phosphate as chromogenic substrate; and (c) β-D-galactosidase (β-D-Gal) with a chromogenic substrate such as p-nitrophenyl-β-D-galactosidase or fluorogenic substrate 4-methylumbelliferyl-β-D-galactosidase.

Numerous other enzyme-substrate combinations are available to those skilled in the art. For a general review of these, see U.S. Pat. No. 4,275,149 and U.S. Pat. No. 4,318,980.

The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

In another embodiment, the humanized anti-CD40 antibody is used unlabeled and detected with a labeled antibody that binds the humanized anti-CD40 antibody.

The antibodies described herein may be employed in any known assay method, such as competitive binding assays, direct and indirect sandwich assays, and immunoprecipitation assays. See, e.g., Zola, *Monoclonal Antibodies: A Manual of Techniques*, pp. 147-158 (CRC Press, Inc. 1987).

Diagnostic Kits

A humanized anti-CD40 antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Therapeutic Uses

In another embodiment, a humanized anti-CD40 antibody disclosed herein is useful in the treatment of various disorders associated with the expression of CD40 as described herein.

The humanized anti-CD40 antibody or agent is administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). The humanized anti-CD40 antibody or agent can be administered, for example, as an infusion or as a bolus. Parenteral infusions include intramuscular, intravenous, intraarterial, intraperitoneal, or subcutaneous administration. In addition, the humanized anti-CD40 antibody is suitably administered by pulse infusion, particularly with declining doses of the antibody. In one aspect, the dosing is given by injections, most preferably intravenous or subcutaneous injections, depending in part on whether the administration is brief or chronic.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 20 mg/kg (e.g., 0.1-15 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is that disclosed in WO 94/04188.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with CD40 expression.

The antibody need not be, but is optionally, formulated with one or more agents currently used to prevent or treat the disorder in question. The effective amount of such other agents depends on the amount of humanized anti-CD40 antibody present in the formulation, the type of disorder or treatment, and other factors discussed above. These are generally used in the same dosages and with administration routes as used hereinbefore or about from 1 to 99% of the heretofore employed dosages.

CD40-Associated Disorders

The anti-CD40 antibodies or agents are useful for treating or preventing a CD40-expressing cancer or an immunological disorder characterized by expression of CD40, e.g., by inappropriate activation of immune cells (e.g., lymphocytes or dendritic cells). Such expression of CD40 can be due to, for example, increased CD40 protein levels on the cells surface and/or altered antigenicity of the expressed CD40. Treatment or prevention of the immunological disorder, according to the methods described herein, is achieved by administering to a subject in need of such treatment or prevention an effective amount of the anti-CD40 antibody or agent, whereby the antibody (i) binds to activated immune cells that express CD40 and that are associated with the disease state and (ii) exerts a cytotoxic, cytostatic, or immunosuppressive effect on the activated immune cells.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions).

(See, e.g., *Fundamental Immunology* (William E. Paul ed., Raven Press, N.Y., 3rd ed. 1993).)

Specific examples of such immunological diseases include the following: rheumatoid arthritis, autoimmune demyelinative diseases (e.g., multiple sclerosis, allergic encephalomyelitis), endocrine opthalmopathy, uveoretinitis, systemic lupus erythematosus, myasthenia gravis, Grave's disease, glomerulonephritis, autoimmune hepatological disorder, inflammatory bowel disease (e.g., Crohn's disease or ulcerative colitis), anaphylaxis, allergic reaction, Sjogren's syndrome, type I diabetes mellitus, primary biliary cirrhosis, Wegener's granulomatosis, fibromyalgia, polymyositis, dermatomyositis, inflammatory myositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, *ascariasis*, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, acute respiratory distress syndrome, pulmonary inflammation, osteoporosis, delayed type hypersensitivity and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of $Th_1$-lymphocytes or $Th_2$-lymphocytes.

In some embodiments, the immunological disorder is a T cell-mediated immunological disorder, such as a T cell disorder in which activated T cells associated with the disorder express CD40. Anti-CD40 antibodies or agents can be administered to deplete such CD40-expressing activated T cells. In a specific embodiment, administration of anti-CD40 antibodies or agents can deplete CD40-expressing activated T cells, while resting T cells are not substantially depleted by the anti-CD40 or agent. In this context, "not substantially depleted" means that less than about 60%, or less than about 70% or less than about 80% of resting T cells are not depleted.

The anti-CD40 antibodies and agents as described herein are also useful for treating or preventing a CD40-expressing cancer. Treatment or prevention of a CD40-expressing cancer, according to the methods described herein, is achieved by administering to a subject in need of such treatment or prevention an effective amount of the anti-CD40 antibody or agent, whereby the antibody or agent (i) binds to CD40-expressing cancer cells and (ii) exerts a cytotoxic or cytostatic effect to deplete or inhibit the proliferation of the CD40-expressing cancer cells.

CD40-expressing cancers that can be treated or prevented by the methods described herein include, for example, leukemia, such as acute leukemia, acute lymphocytic leukemia, acute myelocytic leukemia (e.g., myeloblastic, promyelocytic, myelomonocytic, monocytic, or erythroleukemia), chronic leukemia, chronic myelocytic (granulocytic) leukemia, or chronic lymphocytic leukemia; Polycythemia vera; Lymphoma (e.g., Hodgkin's disease or Non-Hodgkin's disease); multiple myeloma, Waldenstrom's macroglobulinemia; heavy chain disease; solid tumors such sarcomas and carcinomas (e.g., fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, or esophageal carcinoma).

Pharmaceutical Compositions and Administration Thereof

A composition comprising a CD40 binding agent (e.g., an anti-CD40 antibody) can be administered to a subject having or at risk of having an immunological disorder or a CD40-expressing cancer. The invention further provides for the use of a CD40 binding agent (e.g., an anti-CD40 antibody) in the manufacture of a medicament for prevention or treatment of a CD40 expressing cancer or immunological disorder. The term "subject" as used herein means any mammalian patient to which a CD40-binding agent can be administered, including, e.g., humans and non-human mammals, such as primates, rodents, and dogs. Subjects specifically intended for treatment using the methods described herein include humans. The antibodies or agents can be administered either alone or in combination with other compositions in the prevention or treatment of the immunological disorder or CD40-expressing cancer.

Various delivery systems are known and can be used to administer the CD40 binding agent. Methods of introduction include but are not limited to intradermal, intramuscular, intraperitoneal, intravenous, subcutaneous, intranasal, epidural, and oral routes. The CD40 binding agent can be administered, for example by infusion, bolus or injection, and can be administered together with other biologically active agents such as chemotherapeutic agents. Administration can be systemic or local.

In specific embodiments, the CD40 binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-CD40 antibody or agent does not absorb are used.

In other embodiments, the anti-CD40 antibody or agent is delivered in a controlled release system. In one embodiment, a pump may be used (see, e.g., Langer, 1990, *Science* 249: 1527-1533; Sefton, 1989, *CRC Crit. Ref. Biomed. Eng.* 14:201; Buchwald et al., 1980, *Surgery* 88:507; Saudek et al., 1989, *N. Engl. J. Med.* 321:574). In another embodiment, polymeric materials can be used. (See, e.g., *Medical Applications of Controlled Release* (Langer and Wise eds., CRC Press, Boca Raton, Fla., 1974); *Controlled Drug Bioavailability, Drug Product Design and Performance* (Smolen and Ball eds., Wiley, New York, 1984); Ranger and Peppas, 1983, *Macromol. Sci. Rev. Macromol. Chem.* 23:61. See also Levy et al., 1985, *Science* 228:190; During et al., 1989, *Ann. Neurol.* 25:351; Howard et al., 1989, *J. Neurosurg.* 71:105.) Other controlled release systems are discussed, for example, in Langer, supra.

A CD40 binding agent (e.g., an anti-CD40 antibody) can be administered as pharmaceutical compositions comprising a therapeutically effective amount of the binding agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Other suitable pharmaceutical excipients include amino acids (e.g., arginine, histidine, glycine), surfactants (e.g., polysorbates) and sugars and sugar alcohols (e.g., sucrose or sorbitol and other polyols (e.g., trehalose)). The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a CD40 binding agent (e.g., an anti-CD40 antibody) in lyophilized form and (b) a second container containing a pharmaceutically acceptable diluent (e.g., sterile water) for injection. The pharmaceutically acceptable diluent can be used for reconstitution or dilution of the lyophilized anti-CD40 antibody or agent. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the CD40 binding agent (e.g., anti-CD40 antibody) that is effective in the treatment or prevention of an immunological disorder or CD40-expressing cancer can be determined by standard clinical techniques. In addition, in vitro assays may optionally be employed to help identify optimal dosage ranges. The precise dose to be employed in the formulation will also depend on the route of administration, and the stage of immunological disorder or CD40-expressing cancer, and should be decided according to the judgment of the practitioner and each patient's circumstances. Effective doses may be extrapolated from dose-response curves derived from in vitro or animal model test systems.

For example, toxicity and therapeutic efficacy of the anti-CD40 antibody or agent can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A CD40-binding agent (e.g., an anti-CD40 antibody) that exhibits a large therapeutic index is preferred. Where a CD40-binding agent exhibits toxic side effects, a delivery system that targets the CD40-binding agent to the site of affected tissue can be used to minimize potential damage non-CD40-expressing cells and, thereby, reduce side effects.

The data obtained from the cell culture assays and animal studies can be used in formulating a range of dosage for use in humans. The dosage of the CD40 binding agent typically lies within a range of circulating concentrations that include the $ED_{50}$ with little or no toxicity. The dosage may vary within this range depending upon the dosage form employed and the route of administration utilized. For any CD40 binding agent used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Generally, the dosage of an anti-CD40 antibody or CD40 binding agent administered to a patient with an immunological disorder or CD40-expressing cancer is typically about 0.1 mg/kg to about 100 mg/kg of the subject's body weight. The dosage administered to a subject is about 0.1 mg/kg to about 50 mg/kg, about 1 mg/kg to about 30 mg/kg, about 1 mg/kg to about 20 mg/kg, about 1 mg/kg to about 15 mg/kg, or about 1 mg/kg to about 10 mg/kg of the subject's body weight.

Exemplary doses include, but are not limited to, from 1 ng/kg to 100 mg/kg. In some embodiments, a dose is about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 16 mg/kg. The dose can be administered, for example, daily, once per week (weekly), twice per week, thrice per week, four times per week, five times per week, six times per week, biweekly or monthly. In specific embodiments, the dose is about 0.5 mg/kg/week, about 1 mg/kg/week, about 2 mg/kg/week, about 3 mg/kg/week, about 4 mg/kg/week, about 5 mg/kg/week, about 6 mg/kg/week, about 7 mg/kg/week, about 8 mg/kg/week, about 9 mg/kg/week, about 10 mg/kg/week, about 11 mg/kg/week, about 12 mg/kg/week, about 13 mg/kg/week, about 14 mg/kg/week, about 15 mg/kg/week or about 16 mg/kg/week. In some embodiments, the dose ranges from about 1 mg/kg/week to about 15 mg/kg/week.

In some embodiments, the pharmaceutical compositions comprising the CD40 binding agent can further comprise a therapeutic agent, either conjugated or unconjugated to the binding agent. The anti-CD40 antibody or CD40 binding agent can be co-administered in combination with one or more therapeutic agents for the treatment or prevention of immunological disorders or CD40-expressing cancers. For example, combination therapy can include a cytostatic, cytotoxic, or immunosuppressive agent. Combination therapy can also include, e.g., administration of an agent that targets a receptor or receptor complex other than CD40 on the surface of activated lymphocytes, dendritic cells or CD40-expressing cancer cells. An example of such an agent includes a second, non-CD40 antibody that binds to a molecule at the surface of an activated lymphocyte, dendritic cell or CD40-expressing cancer cell. Another example includes a ligand that targets such a receptor or receptor complex. Typically, such an antibody or ligand binds to a cell surface receptor on activated lymphocytes, dendritic cell or CD40-expressing cancer cell and enhances the cytotoxic or cytostatic effect of the anti-CD40 antibody by delivering a cytostatic or cytotoxic signal to the activated lymphocyte, dendritic cell or CD40-expressing cancer cell.

Such combinatorial administration can have an additive or synergistic effect on disease parameters (e.g., severity of a symptom, the number of symptoms, or frequency of relapse).

With respect to therapeutic regimens for combinatorial administration, in a specific embodiment, an anti-CD40 antibody or CD40 binding agent is administered concurrently with a therapeutic agent. In another specific embodiment, the therapeutic agent is administered prior or subsequent to administration of the anti-CD40 antibody or CD40 binding agent, by at least an hour and up to several months, for example at least an hour, five hours, 12 hours, a day, a week, a month, or three months, prior or subsequent to administration of the anti-CD40 antibody or CD40 binding agent.

Useful classes of cytotoxic or immunosuppressive agents include, for example, antitubulin agents, auristatins (e.g., MMAE, or MMAF), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunosuppressive agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE, AEB or AEVB), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, or mitoxantrone.

In some embodiments, the cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to the anti-CD40 antibodies or agents thereof.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in, for example, U.S. Patent Application Publication Nos. 2004-0157782 A1 and 2005-0238649; International Patent Application No. PCT/US03/24209, International Patent Application No. PCT/US02/13435, and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414; the disclosures of which are incorporated by reference herein.

In specific embodiments, the cytotoxic agent is a DNA minor groove binding agent. (See, e.g., U.S. Pat. No. 6,130,237.) For example, in some embodiments, the minor groove binding agent is a CBI compound. In other embodiments, the minor groove binding agent is an enediyne (e.g., calicheamicin).

Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other anti-tubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, *Cancer Res.* 52:127-131).

In some embodiments, the therapeutic agent is not a radioisotope.

In some embodiments, the cytotoxic or immunosuppressive agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscamet, or trifluridine.

In other embodiments, the cytotoxic or immunosuppressive agent is tacrolimus, cyclosporine or rapamycin. In further embodiments, the cytotoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, revlimid, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In additional embodiments, the drug is a humanized anti-HER2 monoclonal antibody; RITUXAN® (rituximab; Genentech, Inc., South San Francisco, CA; a chimeric anti-CD20 monoclonal antibody); OVAREX® (oregovomab; AltaRex Corporation, MA); PANOREX® (edrecolomab; Glaxo Wellcome, NC; a murine IgG2a antibody); ERBITUX® (cetuximab; Imclone Systems Inc., NY; an anti-EGFR IgG chimeric antibody); Vitaxin® (MedImmune, Inc., MD); Campath® I/H (alemtuzumab; Leukosite, MA; a humanized IgG1 antibody); Smart MI95 (Protein Design Labs, Inc., CA; a humanized anti-CD33 IgG antibody); LymphoCide™ (epratuzumab; Immunomedics, Inc., NJ; a humanized anti-CD22 IgG antibody); Smart ID10 (Protein Design Labs, Inc., CA; a humanized anti-HLA-DR antibody); Oncolym® (Techniclone, Inc., CA; a radiolabeled murine anti-HLA-Dr 10 antibody); Allomune™ (BioTransplant, CA; a humanized anti-CD2 mAb); Avastin® (bevacizumab; Genentech, Inc., CA; an anti-VEGF humanized antibody); Epratuzumab (Immunomedics, Inc., NJ and Amgen, CA; an anti-CD22 antibody); and CEAcide (Immunomedics, NJ; a humanized anti-CEA antibody).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti transferrin receptor, p97, MUC1-KLH, CEA, gp100, MART1, Prostate Specific Antigen, IL-2 receptor, CD20, CD52, CD33, CD22, human chorionic gonadotropin, CD38, mucin, P21, MPG, and Neu oncogene product.

In some embodiments, the therapeutic agent is an immunosuppressive agent. The immunosuppressive agent can be, for example, gancyclovir, etanercept, tacrolimus, cyclosporine, rapamycin, cyclophosphamide, azathioprine, mycophenolate mofetil or methotrexate. Alternatively, the immunosuppressive agent can be, for example, a glucocorticoid (e.g., cortisol or aldosterone) or a glucocorticoid analogue (e.g., prednisone or dexamethasone).

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, lonapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK and F-104493, Leo Denmark SR-2566, Tanabe T-757 and Teijin TEI-1338.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the humanized anti-CD40 antibody. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

ATCC Deposits

An ATCC deposit of monoclonal antibody S2C6 was made on May 25, 1999 pursuant to the terms of the Budapest Treaty on the international recognition of the deposit of microorganisms for purposes of patent procedure. The ATCC is located at University Boulevard, Manassas, Virgina 20110-2209, USA. This ATCC deposit was given an accession number of PTA-10. The ATCC is located at 10801 University Boulevard, Manassas, Virgina 20110-2209, USA. Any deposit is provided as a convenience to those of skill in the art and is not an admission that a deposit is required under 35 U.S.C. Section 112. That described herein is not to be limited in scope by the antibody deposited, since the deposited embodiment is intended as a single illustration of certain aspects of the invention and any antibody that is functionally equivalent is within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

The invention is further described in the following examples, which are not intended to limit the scope of the invention. Cell lines described in the following examples were maintained in culture according to the conditions specified by the American Type Culture Collection (ATCC) or Deutsche Sammung von Mikroorganismen und Zellkulturen GmbH, Braunschweig, Germany (DMSZ). Cell culture reagents were obtained from Invitrogen Corp. (Carlsbad, Calif.).

EXAMPLES

Example 1

Production of Humanized Anti-CD40 Antibody

A humanized anti-CD40 antibody was constructed generally by importing the CDRs of the murine anti-CD40 donor antibody into a recipient human antibody. The donor antibody was the murine monoclonal antibody S2C6, described in U.S. Pat. No. 6,838,261, and demonstrated to provide strong, growth-promoting signals to B-lymphocytes. See, e.g., Paulie et. al., 2000, *J. Immunol.* 142:590. Consensus sequences for the human subgroup III heavy chain variable domain (SEQ ID NO:2) and for the human kappa subgroup I light chain variable domain (SEQ ID NO: 13) were obtained, as generally described in Carter et. al., 1992, *Proc. Natl. Acad. Sci. USA* 89:4285; U.S. Pat. No. 6,037,454, and U.S. Pat. No. 6,054,297 to use as the human recipient heavy and light chain domains.

The phagemid pEMX1, described in Cunningham et. al. (1989, *Science* 243:1330-1336), contains a DNA fragment encoding the human consensus Kappa-subgroup I light chain variable domain and a consensus human subgroup III heavy chain variable domain, and is a useful vector for mutagenesis as well as for expression of F(ab)s in *E. coli*. DNA encoding the consensus variable domains is operably linked to an alkaline phosphatase promoter and Shine-dalgarno sequence, derived from a pUC119-based plasmid, pAK2, as described in Carter et al., 1992, *Proc. Natl. Acad. Sci. USA* 89:4285. A unique SpeI restriction site was engineered between the polynucleotides encoding the F(ab) light and heavy chain variable domains. pEMX1 was constructed and used in preparing the humanized antibodies disclosed herein.

A first humanized mAb S2C6 F(ab), referred to as sgn-0, was constructed by importing the CDRs of the murine antibody into the human consensus sequence framework regions by site-directed mutagenesis. Mutagenesis was conducted generally according to the methods described in Kunkel, 1985, *Proc. Natl. Acad. Sci. USA* 82:488. The resulting amino acid sequences of the humanized F(ab) molecule (sgn-0) heavy and light chain variable domains are shown in Table 2 (SEQ ID NO:3 and SEQ ID NO: 14, respectively), and are compared with those of the donor antibody, murine monoclonal antibody S2C6 (mMAb S2C6, also referred to herein as SGN-14; SEQ ID NO: 1 and SEQ ID NO: 12, respectively), and with those of the human consensus sequence recipient antibodies, $HUV_H$ III and $HUV_L\kappa$ I (SEQ ID NO:2 and SEQ ID NO:13, respectively).

Plasmids were transformed into *E. coli* strain XL-1 Blue (Strataene, San Diego, Calif.) for preparation of double and single stranded DNA. Each of the light chain and heavy chain variable domains were completely sequenced using the dideoxynucleotide method (Sequenase, U.S. Biochemical Corp.). Plasmids were transformed into *E. coli* strain 16C9, a derivative of MM294, plated onto LB plates containing 5 μg/ml carbenicillin, and a single colony was selected for protein expression. The 5 ml culture was added to 500 ml AP5-100 μg/ml carbenicillin and allowed to grow for 16 hours in a 4 L baffled shake flask at 37° C. APS media consisted of 1.5 g glucose, 11.0 g Hycase SF, 0.6 g yeast extract (certified), 0.19 g $MgSO_4$ (anhydrous), 1.07 g $NH_4Cl$, 3.73 g KCl, 1.2 g NaCl, 120 ml 1M triethanolamine, pH 7.4, to 1 L water and then sterile filtered through 0.1 μm Sealkeen filter.

Cells were harvested by centrifugation in a 1 L centrifuge bottle (Nalgene) at 3000×g, and the supernatant removed. After freezing for 1 hour, the pellet was resuspended in 25 ml cold 10 mM MES, 10 mM EDTA, pH 5.0 (buffer A). 250 μl of 0.1 M PMSF (Sigma) was added to inhibit proteolysis and 3.5 ml of stock 10 mg/ml hen egg white lysozyme (Sigma) was added to aid lysis of the bacterial cell wall. After gentle shaking on ice for 1 hour, the sample was centrifuged at 40,000×g for 15 minutes. The supernatant was brought to 50 ml with buffer A and loaded onto a 2 ml DEAE column equilibrated with buffer A. The flow-through was then applied to a protein G-Sepharose CL-4B column (Pharmacia) (0.5 ml bed volume) equilibrated with buffer A. The column was washed with 10 ml buffer A and eluted with 3 ml 0.3 M glycine, pH 3.0, into 1.25 ml of 1M TRIS, pH8.0. The F(ab) was then buffer exchanged into PBS using a Centricon-30 filter (Amicon) and concentrated to a final volume of 0.5 ml. SDS PAGE gels of the F(ab) were run to ascertain purity and the molecular weight was verified by electrospray mass spectrometry.

The humanized antibody, sgn-0, demonstrated a significantly diminished binding affinity for CD40 immobilized on microtiter plates, as compared with that of the parent, murine antibody.

TABLE 2

Example 2: Preparation of Humanized Anti-CD40
Varient Antibodies

Variable Heavy
Ab/SEQ ID NO:

```
                    10         20         30         40         50
SGN-14/1    EVQLQQSGPD LVKPGASVKT SCKASGYSFT GYYIHWVKQS HGKSLEWIGR
sgn-0/3     EVQLVESGGG LVQPGGSLRL SCAASGYSFT GYYIHWVRQA PGKGLEWVAR
HumVHIII/2  EVQLVESGGG LVQPGGSLRL SCAASGFTFS SYAMSWVRQA PGKGLEWVAV
                                      CDR-H1

60         70         80         90        100
SGN-14/1    VIPNNGGTSY NQKFKGKAIL TVDKSSSTAY MELRSLTSED SAVYYCAREG
sgn-0/3     VIPNNGGTSY NQKFKGRFTI SRDNSKNTLY LQMNSLRAED TAVYYCAREG
HumVHIII/2  ISGDGGSTYY ADSVKGRFTI SRDNSKNTLY LQMNSLRAED TAVYYCARGR
                CDR-H2

110
SGN-14/1    I---YWWGHG TTLTVS
sgn-0/3     I---YWWGQG TLVTVS
HumVHIII/2  GGGSDYWGQG TLVTVS
                CDR-H3
```

Variable Light
Ab/SEQ ID NO:

```
                    10         20         30         40         50
SGN-14/12   DVVVTQTPLS LPVSLGAQAS ISCRSSQSLV HSNGNTFLHW YLQKPGQSPK
sgn-0/14    DIQMTQSPSS LSASVGDRVT ITCRSSQSLV HSNGNTFLHW YQQKPGKAPK
HumKI/13    DIQMTQSPSS LSASVGDRVT ITCRASQSIS NYL-----AW YQQKPGKAPK
                                      CDR-L1

60         70         80         90        100
SGN-14/12   LLIYTVSNRF SGVPDRFSGS GSGTDFTLKI SRVEAEDLGV YFCSQTTHVP
sgn-0/14    LLIYTVSNRF SGVPSRFSGS GSGTDFTLTI SSLQPEDFAT YYCSQTTHVP
HumKI/13    LLIYAASSLE SGVPSRFSGS GSGTDFTLTI SSLQPEDFAT YYCQQYNSLP
                CDR-L2                                      CDR-L3

110
SGN-14/12   WTFGGGTKLE IQR
sgn-0/14    WTFGQGTKVE IKR
HumKI/13    WTFGQGTKVE IKR
```

A series of mutations were made to the template humanized antibody, sgn-0, prepared as described for Example 1. Specific mutations were made to the DNA encoding the light and heavy chain variable domains of sgn-0 by site directed mutagenesis, and the sequences of the variants produced from the template molecule are listed below in Tables 3 and 4.

Antibodies constructed using these variant light and heavy chain variable domains were analyzed for binding activity. Each antibody was diluted to equivalent concentrations, and then serially diluted. The diluted antibodies were assayed for binding to CD40 immobilized on microassay plates. Affinity binding data for the variant antibodies are shown below in Table 5. Antibodies showing binding activity approaching that of the parent murine antibody were sgn-14, sgn-18, sgn-19, sgn-22, sgn-23, sgn-26, and sgn-27, with variants sgn-14, sgn-18, sgn-26, and sgn-27 more closely approaching that of the parent murine antibody, SGN-14, and variant sgn-26 showing the best performance in these assays.

TABLE 3

Heavy Chain Variable Domain

Ab/SEQ ID NO

```
                   10         20         30         40         50
sgn-0/3    EVQLVESGGG LVQPGGSLRL SCAASGYSFT GYYIHWVRQA PGKGLEWVAR
sgn-1/4    EVQLVESGGG LVQPGGSLRL SCAASGYSFT GYYIHWVRQA PGKGLEWVAR
agn-2/5    EVQLVESGGG LVQPGGSLRL SCAASGYSFT GYYIHWVRQA PGKGLEWVAR
sgn-4/6    EVQLVESGGG LVQPGGSLRL SCAASGYSFT GYYIHWVRQA PGKGLEWVAR
sgn-14/7   EVQLVESGGG LVQPGGSLRL SCAASGYSFT GYYIHWVRQA PGKGLEWVAR
sgn-15/8   EVQLVESGGG LVQPGGSLRL SCAASGYSFT GYYIHWVRQA PGKGLEWVAR
sgn-16/9   EVQLVESGGG LVQPGGSLRL SCAASGYSFT GYYIHWVRQA PGKGLEWVAR
sgn-17/6   EVQLVESGGG LVQPGGSLRL SCAASGYSFT GYYIHWVRQA PGKGLEWVAR
sgn-18/6   EVQLVESGGG LVQPGGSLRL SCAASGYSFT GYYIHWVRQA PGKGLEWVAR
sgn-19/7   EVQLVESGGG LVQPGGSLRL SCAASGYSFT GYYIHWVRQA PGKGLEWVAR
sgn-22/10  EVQLVESGGG LVQPGGSLRL SCAASGYSFT GYYIHWVRQA PGKGLEWVAR
sgn-23/11  EVQLVESGGG LVQPGGSLRL SCAASGYSFT GYYIHWVRQA PGKGLEWVAR
sgn-26/10  EVQLVESGGG LVQPGGSLRL SCAASQYSFT GYYIHWVRQA PGKGLEWVAR
sgn-27/11  EVQLVESGGG LVQPGGSLRL SCAASGYSFT GYYIHWVRQA PGKGLEWVAR
                                      CDR-H1
```

TABLE 3-continued

Heavy Chain Variable Domain

Ab/SEQ ID NO

```
                60           70           80           90           100
sgn-0/3     VIPNNGGTSY  NQKFKGRFTI  SRDNSKNTLY  LQMNSLRAED  TAVYYCAREG
sgn-1/4     VIPNNGGTSY  NQKFKGRFTI  SVDNSKNTLY  LQMNSLRAED  TAVYYCAREG
sgn-2/5     VIPNNGGTSY  NQKFKGRFTI  SRDKSKNTLY  LQMNSLRAED  TAVYYCAREG
sgn-4/6     VIPNNGGTSY  NQKFKGRATL  SVDNSKNTAY  LQMNSLRAED  TAVYYCAREG
sgn-14/7    VIPNNGGTSY  NQKFKGRFTL  SVDNSKNTAY  LQMNSLRAED  TAVYYCAREG
sgn-15/8    VIPNNGGTSY  NQKFKGRATI  SVDNSKNTAY  LQMNSLRAED  TAVYYCAREG
sgn-16/9    VIPNNGGTSY  NQKFKGRATL  SVDNSKNTLY  LQMNSLRAED  TAVYYCAREG
sgn-17/6    VIPNNGGTSY  NQKFKGRATL  SVDNSKNTAY  LQMNSLRAED  TAVYYCAREG
Sgn-18/6    VIPNNGGTSY  NQKFKGRATL  SVDNSKNTAY  LQMNSLRAED  TAVYYCAREG
sgn-19/7    VIPNNGGTSY  NQKFKGRFTL  SVDNSKNTAY  LQMNSLRAED  TAVYYCAREG
sgn-22/10   VIPNAGGTSY  NQKFKGRFTL  SVDNSKNTAY  LQMNSLRAED  TAVYYCAREG
sgn-23/11   VIPNQGGTSY  NQKFKGRFTL  SVDNSKNTAY  LQMNSLRAED  TAVYYCAREG
sgn-26/10   VIPNAGGTSY  NQKFKGRFTL  SVDNSKNTAY  LQMNSLRAED  TAVYYCAREG
sgn-27/11   VIPNQGGTSY  NQKFKGRFTL  SVDNSKNTAY  LQMNSLRAED  TAVYYCAREG
                CDR-H2

110
sgn-0/3     I---  YWWGQGTLV  TVS
sgn-1/4     I---  YWWGQGTLV  TVS
sgn-2/5     I---  YWWGQGTLV  TVS
sgn-4/6     I---  YWWGQGTLV  TVS
sgn-14/7    I---  YWWGQGTLV  TVS
sgn-15/8    I---  YWWGQGTLV  TVS
sgn-16/9    I---  YWWGQGTLV  TVS
sgn-17/6    I---  YWWGQGTLV  TVS
sgn-18/6    I---  YWWGQGTLV  TVS
sgn-19/7    I---  YWWGQGTLV  TVS
sgn-22/10   I---  YWWGQGTLV  TVS
sgn-23/11   I---  YWWGQGTLV  TVS
sgn-26/10   I---  YWWGQGTLV  TVS
sgn-27/11   I---  YWWGQGTLV  TVS
            CDR-H3
```

TABLE 4

Light Chain Variable Domain

Ab/SEQ ID NO

```
                10          20           30           40           50
sgn-0/14    DIQMTQSPSS  LSASVGDRVT  ITCRSSQSLV  HSNGNTFLHW  YQQKPGKAPK
sgn-1/14    DIQMTQSPSS  LSASVGDRVT  ITCRSSQSLV  HSNGNTFLHW  YQQKPGKAPK
sgn-2/14    DIQMTQSPSS  LSASVGDRVT  ITCRSSQSLV  HSNGNTFLHW  YQQKPGKAPK
sgn-4/14    DIQMTQSPSS  LSASVGDRVT  ITCRSSQSLV  HSNGNTFLHW  YQQKPGKAPK
sgn-14/14   DIQMTQSPSS  LSASVGDRVT  ITCRSSQSLV  HSNGNTFLHW  YQQKPGKAPK
sgn-15/14   DIQMTQSPSS  LSASVGDRVT  ITCRSSQSLV  HSNGNTFLHW  YQQKPGKAPK
sgn-16/14   DIQMTQSPSS  LSASVGDRVT  ITCRSSQSLV  HSNGNTFLHW  YQQKPGKAPK
sgn-17/15   DVQVTQSPSS  LSASVGDRVT  ITCRSSQSLV  HSNGNTFLHW  YQQKPGKAPK
sgn-18/16   DIQMTQSPSS  LSASVGDRVT  ITCRSSQSLV  HSNGNTFLHW  YQQKPGKAPK
sgn-19/16   DIQMTQSPSS  LSASVGDRVT  ITCRSSQSLV  HSNGNTFLHW  YQQKPGKAPK
sgn-22/14   DIQMTQSPSS  LSASVGDRVT  ITCRSSQSLV  HSNGNTFLHW  YQQKPGKAPK
sgn-23/14   DIQMTQSPSS  LSASVGDRVT  ITCRSSQSLV  HSNGNTFLHW  YQQKPGKAPK
sgn-26/16   DIQMTQSPSS  LSASVGDRVT  ITCRSSQSLV  HSNGNTFLHW  YQQKPGKAPK
sgn-27/16   DIQMTQSPSS  LSASVGDRVT  ITCRSSQSLV  HSNGNTFLHW  YQQKPGKAPK
                                        CDR-L1

60          70           80           90           100
sgn-0/14    LLIYTVSNRF  SGVPSRFSGS  GSGTDFTLTI  SSLQPEDFAT  YYCSQTTHVP
sgn-1/14    LLIYTVSNRF  SGVPSRFSGS  GSGTDFTLTI  SSLQPEDFAT  YYCSQTTHVP
sgn-2/14    LLIYTVSNRF  SGVPSRFSGS  GSGTDFTLTI  SSLQPEDFAT  YYCSQTTHVP
agn-4/14    LLIYTVSNRF  SGVPSRFSGS  GSGTDFTLTI  SSLQPEDFAT  YYCSQTTHVP
sgn-14/14   LLIYTVSNRF  SGVPSRFSGS  GSGTDFTLTI  SSLQPEDFAT  YYCSQTTHVP
sgn-15/14   LLIYTVSNRF  SGVPSRFSGS  GSGTDFTLTI  SSLQPEDFAT  YYCSQTTHVP
sgn-16/14   LLIYTVSNRF  SGVPSRFSGS  GSGTDFTLTI  SSLQPEDFAT  YYCSQTTHVP
sgn-17/15   LLIYTVSNRF  SGVPSRFSGS  GSGTDFTLTI  SSLQPEDFAT  YYCSQTTHVP
sgn-18/16   LLIYTVSNRF  SGVPSRFSGS  GSGTDFTLTI  SSLQPEDFAT  YFCSQTTHVP
sgn-19/16   LLIYTVSNRF  SGVPSRFSGS  GSGTDFTLTI  SSLQPEDFAT  YFCSQTTHVP
sgn-22/14   LLIYTVSNRF  SGVPSRFSGS  GSGTDFTLTI  SSLQPEDFAT  YYCSQTTHVP
sgn-23/14   LLIYTVSNRF  SGVPSRFSGS  GSGTDFTLTI  SSLQPEDFAT  YYCSQTTHVP
sgn-26/16   LLIYTVSNRF  SGVPSRFSGS  GSGTDFTLTI  SSLQPEDFAT  YFCSQTTHVP
sgn-27/16   LLIYTVSNRF  SGVPSRFSGS  GSGTDFTLTI  SSLQPEDFAT  YFCSQTTHVP
                CDR-L2                                         CDR-L3
```

TABLE 4-continued

| Light Chain Variable Domain | |
|---|---|
| Ab/SEQ ID NO | |
| | 110 |
| sgn-0/14 | WTFGQGTKVE IKR |
| sgn-1/14 | WTFGQGTKVE IKR |
| sgn-2/14 | WTFGQGTKVE IKR |
| sgn-4/14 | WTFGQGTKVE IKR |
| sgn-14/14 | WTFGQGTKVE TKR |
| sgn-15/24 | WTFGQGTKVE IKR |
| sgn-16/14 | WTFGQGTKVE IKR |
| sgn-17/15 | WTFGQGTKVE IKR |
| sgn-18/16 | WTFGQGTKVE IKR |
| sgn-19/16 | WTFGQGTKVE IKR |
| sgn-22/14 | WTFGQGTKVE IKR |
| sgn-23/14 | WTFGQGTKVE IKR |
| sgn-26/16 | WTFGQGTKVE IKR |
| sgn-27/16 | WTFGQGTKVE IKR |

TABLE 5

| Antibody | Heavy Chain Variable Domain | Light Chain Variable Domain | Binding Data 1 | Binding Data 2 | Binding Data 3 |
|---|---|---|---|---|---|
| SGN-14 | SEQ ID NO: 1 Donor | SEQ ID NO: 12 Donor | 1.00 | 1.33 | 1.16 |
| hu sgn-0 | SEQ ID NO: 3 Template | SEQ ID NO: 14 Template | 75.31 | 75.31 | — |
| hu sgn-1 | SEQ ID NO: 4 R72V | SEQ ID NO: 14 Template | 23.63 | 19.31 | — |
| hu sgn-2 | SEQ ID NO: 5 N74K | SEQ ID NO: 14 Template | 471.37 | 370.87 | — |
| hu sgn-4 | SEQ ID NO: 6 F68A I70L R72V L79A | SEQ ID NO: 14 Template | 2.23 1.83 3.12 1.41 | 2.46 | — |
| hu sgn-14 | SEQ ID NO: 7 I70L R72V L79A | SEQ ID NO: 14 Template | 1/11 0.86 0.77 | 0.69 0.77 | — |
| hu sgn-15 | SEQ ID NO: 8 F68A R72V L79A | SEQ ID NO: 14 Template | 10.54 4.67 | 2.71 | — |
| hu sgn-16 | SEQ ID NO: 9 F68A I69L R72V | SEQ ID NO: 14 Template | 44.00 9.78 7.99 | 1.82 1.83 | — |
| hu sgn-17 | SEQ ID NO: 6 F68A I70L R72V L79A | SEQ ID NO: 15 I2V M4V | 3.60 1.76 | 3.56 | — |
| hu sgn-18 | SEQ ID NO: 6 F68A I70L R72V L79A | SEQ ID NO: 16 Y92F | 0.96 0.67 | 1.03 | — |
| hu sgn-19 | SEQ ID NO: 7 I70L R72V L79A | SEQ ID NO: 16 Y92F | 0.481 1.06 0.92 1.14 | 0.501 0.98 | — |
| hu sgn-22 | SEQ ID NO: 10 N55A I70L R72V L79A | SEQ ID NO: 14 Template | 1.44 1.41 1.80 0.93 | 0.84 | — |
| hu sgn-23 | SEQ ID NO: 11 N55Q I70L R72V L79A | SEQ ID NO: 14 Template | 2.11 1.58 2.38 0.72 | 0.90 | — |
| hu sgn-26 | SEQ ID NO: 10 N55A I70L R72V L79A | SEQ ID NO: 16 Y92F | 0.92 1.02 1.02 1.06 | 0.92 | — |
| hu sgn-27 | SEQ ID NO: 11 N55Q I70L R72V L79A | SEQ ID NO: 16 Y92F | 1.04 1.03 0.94 0.83 | 1.40 | — |

Example 3

In Vitro Cytotoxic Activity of Humanized Anti-CD40 Antibody

CD40⁺ and CD138⁺⁺ human multiple myeloma cell lines, MM.1S, which is dexamethasone sensitive, and MM.1R, which is dexamethasone resistant, as well as freshly isolated tumor cells (CD40⁺, CD138⁺) from two multiple myeloma patients, were treated with increasing concentrations (0-100 µg/ml) of humanized S2C6 antibody for 48 hr. DNA synthesis was measured by ³[H]-thymidine uptake. The results indicated that humanized S2C6 antibody did not stimulate proliferation of MM.1S, MM.1R, or the tumor cells from the two patients (p>0.1).

To further define the cytotoxic effect of humanized S2C6 antibody against these cells, cultures of MM.1S and MM.1R were treated for 6 hr with humanized S2C6 antibody (10 µg/ml) and then cocultured with the de novo protein synthesis inhibitor cycloheximide (0.2 µg/ml) for an additional 48 hr. Cell viability was assayed using the reduction 3-(4,5-dimethylthiozol-2-yl)-2,5-diphenyltetrazolium bromide (MTT) as the indicator. Treatment with humanized S2C6 antibody and cycloheximide triggered 50-60% cell killing in both cell lines, whereas treatment with isotype control Ig alone, with or without cycloheximide, did not induce cytotoxicity. The humanized S2C6 antibody triggered 20-30% cell cytotoxicity in the two patient tumor cell cultures, which was significantly enhanced in the presence of cycloheximide at a nontoxic dose (0.2 µg/ml).

Example 4

Anti-Tumor Activity of Humanized Anti-CD40 Antibody

The anti-tumor activity of the humanized anti-CD40 antibody was assayed in a SCID mouse lymphoma xenograph model. Five million Ramos tumor cells were injected subcutaneously into SCID mice (10/group) thirteen days prior to starting drug treatment. Murine anti-CD40 antibody or the humanized S2C6 was given intra-peritoneally 3 times per week (4 mg/kg/dose) with 8 or 5 doses administered. Mice were examined for tumor growth, and tumor volume was measured weekly during the 14-day study period. The results in FIG. 2 show a nearly 9-fold increase in the growth of tumors in control mice, whereas over the same time period, tumor growth in mice treated with either murine anti-CD40 antibody or humanized S2C6 was negligible. The data demonstrate that the humanized antibody was as effective as the murine anti-CD40 antibody in suppressing tumor growth in this B lymphoma xenograph model.

Example 5

Prolonged Survival by Humanized Anti-CD40 Antibody

Figure 3:
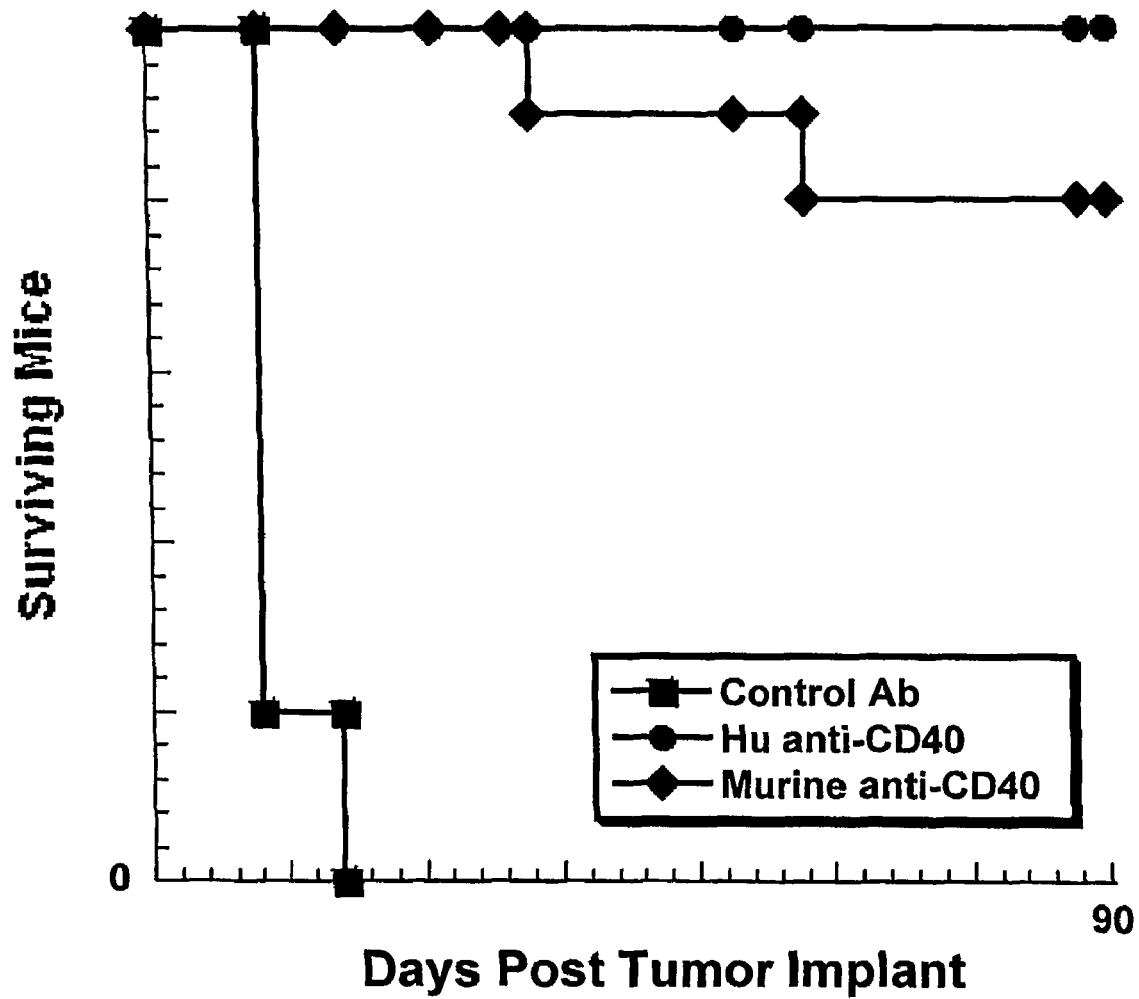
FIG. 3 shows the effect of treatment with a control antibody, a murine anti-CD40 antibody, and a humanized anti-CD40 antibody, on survival of tumor-bearing mice.

The efficacy of the humanized anti-CD40 antibody on survival of tumor-bearing mice was assayed in a SCID mouse lymphoma xenograph model. SCID mice (10/group) were inoculated intravenously with one million Ramos tumor cells three days prior to antibody treatment. Mice were treated with murine or humanized anti-CD40 antibody, or an Ig control, adminstered intraperitoneally two times per week (4 mg/kg/dose) for a total of five doses. The mouse cages were examined daily for mortality. The results shown in FIG. 3 show that none of the mice treated with a control antibody survived beyond day 34 post tumor inoculation, whereas eight of the ten mice treated with murine anti-CD40 antibody and all ten mice treated with the humanized anti-CD40 antibody remained alive at even 90 days after tumor implant. The data demonstrate that the humanized antibody was as effective as the murine anti-CD40 antibody in prolonging survival of SCID mice in this B lymphoma xenograph model.

Various references, including patent applications, patents, and scientific publications, are cited herein, the disclosures of which are incorporated herein by reference in their entireties. Citation or identification of any reference herein shall not be construed as an admission that such reference is available as prior art to the present invention.

The application of the teachings disclosed herein is not to be limited in scope by the specific embodiments described herein. Indeed, various modifications will be within the capabilities of one having ordinary skill in the art in light of the teachings contained herein and accompanying examples. Such modifications are intended to fall within the scope of the appended claims.

---

What is claimed is:

1. An isolated unconjugated antibody or antigen-binding fragment that specifically binds to human CD40, comprising a humanized heavy chain variable domain and a humanized light chain variable domain, wherein the heavy chain variable domain and the light chain variable domain comprise the amino acid sequences of SEQ ID NO:10 and SEQ ID NO:16, respectively.

2. The antibody or antigen-binding fragment of claim 1, further comprising a human IgG constant region.

3. The antibody or antigen-binding fragment of claim 2, wherein the isotype of the IgG constant region is IgG1, IgG2, IgG3, or IgG4.

4. The antibody or antigen-binding fragment of claim 3, wherein the isotype of the IgG constant region is IgG1.

5. The antibody or antigen-binding fragment of claim 1, further comprising a light chain constant domain.

6. The antibody or antigen-binding fragment of claim 5, wherein the light chain constant domain is a kappa constant domain.

7. The antibody of claim 1, wherein the antibody further comprises a human immunoglobulin constant region.

8. The antibody of claim 7, comprising the heavy chain and the light chain amino acid sequences set forth in SEQ ID NO:19 and SEQ ID NO:22, respectively.

9. The antibody or antigen-binding fragment of claim 1, which is an antigen-binding antibody fragment.

10. The antigen-binding fragment of claim 9, wherein the antibody fragment is a Fab, a Fab', a F(ab')$_2$, a Fv fragment, a diabody, a single-chain antibody, an scFv fragment or an scFv-Fc.

11. A kit comprising in a container the antibody or antigen-binding fragment of claim 1, and optionally instructions for using the antibody to detect CD40 protein in a biological sample.

12. A method for inhibiting the growth of cells expressing human CD40 antigen, comprising administering the antibody or antigen-binding fragment of claim 1 to the cells, which antibody or antigen-binding fragment specifically binds to the human cell surface CD40 antigen, wherein the binding of the antibody or antigen-binding fragment to the CD40 antigen inhibits the growth or differentiation of the cells.

13. A method for treating a subject having a CD40-expressing cancer, comprising administering to the subject the antibody or antigen-binding fragment of claim 1, which antibody or antigen-binding fragment specifically binds to human CD40, wherein the binding of the antibody or antigen-binding fragment to CD40 inhibits the growth or differentiation of cells of the CD40-expressing cancer.

14. The method of claim 13, wherein the cells of the CD40-expressing cancer are B lymphoblastoid cells, pancreatic cells, lung cells, breast cells, ovarian cells, colon cells, prostate cells, skin cells, head and neck cells, bladder cells, bone cells or kidney cells.

15. The method of claim 13, wherein the CD40-expressing cancer is chronic lymphocytic leukemia, Burkitt's lymphoma, multiple myeloma, a T cell lymphoma, Non-Hodgkin's Lymphoma, Hodgkin's Disease, Waldenstrom's macroglobulinemia or Kaposi's sarcoma.

16. A method for inducing depletion of peripheral B cells, comprising administering to the cells the antibody or antigen-binding fragment of claim 1, which antibody or antigen-binding fragment specifically binds to a human cell surface CD40 antigen, wherein the binding of the antibody or antigen-binding fragment to the CD40 antigen induces depletion of the cells.

17. The method of claim 16, wherein the antibody or antigen-binding fragment is administered to a subject having an immune disorder.

18. The method of claim 17, wherein the immune disorder is rheumatoid arthritis or systemic lupus erythematosus.

19. The antibody or antigen-binding fragment of claim 1, wherein the antibody or antigen-binding fragment competes for binding with monoclonal antibody S2C6 that is secreted by a hybridoma having ATCC Accession No. PTA-110, wherein the monoclonal antibody S2C6 comprises a heavy chain variable domain and a light chain variable domain comprising the amino acid sequences of SEQ ID NO:1 and SEQ ID NO:12, respectively.

20. A pharmaceutical composition comprising:
  (i) the antibody or antigen-binding fragment of claim 1; and
  (ii) a pharmaceutically acceptable excipient.

* * * * *

UNITED STATES PATENT AND TRADEMARK OFFICE
CERTIFICATE OF CORRECTION

PATENT NO. : 8,303,955 B2
APPLICATION NO. : 11/913305
DATED : November 6, 2012
INVENTOR(S) : Leonard G. Presta et al.

It is certified that error appears in the above-identified patent and that said Letters Patent is hereby corrected as shown below:

On the Title Page:

Item (75) Inventors: please delete "Svetlana O. Doronina"

Signed and Sealed this
Twenty-ninth Day of January, 2013

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,303,955 B2 | Page 1 of 1 |
| APPLICATION NO. | : 11/913305 | |
| DATED | : November 6, 2012 | |
| INVENTOR(S) | : Presta et al. | |

It is certified that error appears in the above-identified patent and that said Letters Patent is hereby corrected as shown below:

On the Title Page:

Item [73] Assignee: please insert -- Genentech, Inc., South San Francisco, CA (US) --

Signed and Sealed this
Twenty-second Day of April, 2014

Michelle K. Lee
*Deputy Director of the United States Patent and Trademark Office*